US010676530B2

(12) United States Patent
Stahl et al.

(10) Patent No.: US 10,676,530 B2
(45) Date of Patent: Jun. 9, 2020

(54) METHODS FOR TREATING ALLERGY AND ENHANCING ALLERGEN-SPECIFIC IMMUNOTHERAPY BY ADMINISTERING AN ANTIBODY TO IL-4 RECEPTOR

(71) Applicant: Regeneron Pharmaceuticals, Inc., Tarrytown, NY (US)

(72) Inventors: Neil Stahl, Carmel, NY (US); Jamie M. Orengo, Cortlandt Manor, NY (US); Andrew J. Murphy, Croton-on-Hudson, NY (US); Namita Gandhi, New York, NY (US); Neil Graham, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 56 days.

(21) Appl. No.: 15/842,868

(22) Filed: Dec. 14, 2017

(65) Prior Publication Data
US 2018/0094070 A1   Apr. 5, 2018

Related U.S. Application Data

(62) Division of application No. 14/294,544, filed on Jun. 3, 2014, now Pat. No. 10,392,439.

(60) Provisional application No. 61/830,919, filed on Jun. 4, 2013.

(51) Int. Cl.
  A61K 39/395    (2006.01)
  C07K 16/28     (2006.01)
  A61K 45/06     (2006.01)
  A61P 37/02     (2006.01)
  A61K 39/00     (2006.01)

(52) U.S. Cl.
  CPC ........ *C07K 16/2866* (2013.01); *A61K 39/395* (2013.01); *A61K 45/06* (2013.01); *A61P 37/02* (2018.01); *A61K 2039/505* (2013.01); *A61K 2039/577* (2013.01)

(58) Field of Classification Search
  CPC .................................................. A61K 39/395
  See application file for complete search history.

(56) References Cited

U.S. PATENT DOCUMENTS

| 5,599,905 A | 2/1997 | Mosley |
| 5,714,146 A | 2/1998 | Lewis |
| 5,717,072 A | 2/1998 | Mosley |
| 5,856,296 A | 1/1999 | Mosley |
| 5,985,280 A | 11/1999 | Ritter |
| 6,156,877 A | 12/2000 | Ritter |
| 6,391,581 B1 | 5/2002 | Mosley |
| 6,548,655 B1 | 4/2003 | Mosley |
| 6,716,587 B2 | 4/2004 | Mosley |
| 7,141,653 B2 | 11/2006 | Greenfeder |
| 7,186,809 B2 | 3/2007 | Pluenneke |
| 7,317,090 B2 | 1/2008 | Mosley |
| 7,422,742 B2 | 9/2008 | Greenfeder |
| 7,531,169 B2 | 5/2009 | Singh |
| 7,605,237 B2 | 10/2009 | Stevens |
| 7,608,693 B2 | 10/2009 | Martin |
| 7,794,717 B2 | 9/2010 | Stevens |
| 8,030,003 B2 | 10/2011 | Rothenberg |
| 8,075,887 B2 | 12/2011 | Martin |
| 8,075,897 B2 | 12/2011 | Spertini |
| 8,092,802 B2 | 1/2012 | Stevens |
| 8,092,804 B2 | 1/2012 | Eriksson et al. |
| 8,252,284 B2 | 8/2012 | Singh |
| 8,324,192 B2 | 12/2012 | Dohil |
| 8,337,839 B2 | 12/2012 | Martin |
| 8,338,135 B2 | 12/2012 | Stevens |
| 8,497,528 B2 | 7/2013 | Lee |
| 8,604,171 B2 | 12/2013 | Singh |
| 8,637,239 B2 | 1/2014 | Furuta |
| 9,290,574 B2 | 3/2016 | Kostic |
| 9,415,015 B2* | 8/2016 | Jacobi ............... A61K 9/0056 |
| 10,392,439 B2* | 8/2019 | Stahl .................. A61P 37/02 |
| 10,485,844 B2 | 11/2019 | Radin |
| 2003/0103938 A1 | 6/2003 | Jinquan |
| 2003/0113387 A1 | 6/2003 | Tsuchida et al. |
| 2005/0031609 A1 | 2/2005 | Hultsch |
| 2005/0074462 A1 | 4/2005 | Holmgren |
| 2005/0118176 A1 | 6/2005 | Mosley |
| 2005/0255532 A1 | 11/2005 | Ruben |
| 2005/0282181 A1 | 12/2005 | Yan |

(Continued)

FOREIGN PATENT DOCUMENTS

| EP | 0604693 | 7/1994 |
| EP | 0367566 | 5/1997 |

(Continued)

OTHER PUBLICATIONS

European Notice of Opposition in Application 13765844.9, dated Feb. 22, 2019, 34 pages.
Nguyen, Tran Hoai et al., "Future Forms of Immunotherapy and Immunomodulators in Allergic Disease", Immunol Allergy Clin N Am 31 (2011); 343-365.
Antoniu, Sabina, "Pitrakinra, a Dual IL-4R/IL-13 Antagonist for the Potential Treatment of Asthma and Eczema", Current Opinion in Investigational Drugs 2010 11 (11): 1286-1294.
International Investigative Dermatology, Edinburgh, Conference Posters, May 8-11, 2013, 4 pages.
Abstracts, "Human Clinical Research and Therapeutics", Journal of Investigative Dermatology vol. 133, Supplement 1, (2013), pp. S159-S190, Abstracts 1042, and 1048 to 1050, http://apps.webofknowledge.com/full_record.do?product=WOS&search_mode=GeneralSearch&qid=2&SID=E6MDFsiCnXC9MfROx21&page=1&doc=1, 32 pages.

(Continued)

*Primary Examiner* — Prema M Mertz
(74) *Attorney, Agent, or Firm* — Merchant & Gould P.C.

(57) ABSTRACT

The present invention provides methods for treating, preventing or reducing the severity of allergic reactions. The present invention also provides methods for enhancing the efficacy and/or safety of an allergen-specific immunotherapy (SIT) regimen. The methods of the present invention comprise administering to a subject in need thereof a therapeutic composition comprising an interleukin-4 receptor (IL-4Rα) antagonist such as an anti-IL-4Rα antibody.

24 Claims, 13 Drawing Sheets

Specification includes a Sequence Listing.

(56) References Cited

U.S. PATENT DOCUMENTS

| | | |
|---|---|---|
| 2006/0013811 A1 | 1/2006 | Dina |
| 2007/0041976 A1 | 2/2007 | Pluenneke |
| 2007/0274996 A1 | 11/2007 | Carter |
| 2008/0054606 A1 | 5/2008 | Eriksson |
| 2009/0074793 A1 | 3/2009 | Martin |
| 2009/0098142 A1 | 4/2009 | Kasaian |
| 2009/0264392 A1 | 10/2009 | Wamdahl |
| 2010/0047254 A1 | 2/2010 | Martin |
| 2011/0195500 A1 | 8/2011 | Rothenberg |
| 2012/0004205 A1 | 1/2012 | Rothenberg |
| 2012/0052072 A1 | 3/2012 | Martin |
| 2012/0164080 A1 | 6/2012 | Hill |
| 2012/0207815 A1 | 8/2012 | Benhamou |
| 2013/0052190 A1 | 2/2013 | Collins |
| 2013/0078675 A1 | 3/2013 | Martin |
| 2013/0324435 A1 | 12/2013 | Rothenberg |
| 2014/0072583 A1 | 3/2014 | Ardeleanu |
| 2014/0187523 A1 | 7/2014 | Dohil |
| 2014/0271681 A1 | 9/2014 | Martin |
| 2014/0356372 A1 | 12/2014 | Stahl |
| 2015/0185228 A1 | 7/2015 | Reisacher |
| 2015/0246973 A1 | 9/2015 | Graham |
| 2016/0152718 A1 | 6/2016 | Kostic |
| 2017/0333557 A1 | 11/2017 | Ardeleanu |
| 2018/0078603 A1 | 3/2018 | Radin |
| 2018/0094069 A1 | 4/2018 | Stahl |
| 2018/0179288 A1 | 6/2018 | Martin et al. |
| 2019/0040126 A1 | 2/2019 | Radin |
| 2019/0183973 A1 | 6/2019 | Hamilton |
| 2019/0345253 A1 | 11/2019 | Bansal |
| 2019/0367622 A1 | 12/2019 | Graham |

FOREIGN PATENT DOCUMENTS

| | | |
|---|---|---|
| EP | 1113818 B1 | 5/2006 |
| EP | 2022507 A1 | 2/2009 |
| EP | 1527100 | 7/2009 |
| JP | 05-246874 | 9/1993 |
| JP | 2006-131623 | 5/2006 |
| JP | 2016521713 A | 7/2016 |
| RU | 2162711 | 2/2001 |
| RU | 2453303 C1 | 6/2012 |
| WO | 1992/19259 | 11/1992 |
| WO | 1994/14975 | 7/1994 |
| WO | 2001/092340 | 12/2001 |
| WO | 2003/048083 | 6/2003 |
| WO | 2005/047331 | 5/2005 |
| WO | 2005/085284 | 9/2005 |
| WO | 2006/003407 | 1/2006 |
| WO | 2006/072564 | 7/2006 |
| WO | 2006/083390 | 8/2006 |
| WO | 2008/054606 | 5/2008 |
| WO | 2009/124954 | 10/2009 |
| WO | 2010/053751 | 5/2010 |
| WO | 2010/065557 | 6/2010 |
| WO | 2010/120524 | 10/2010 |
| WO | 2011/026966 | 3/2011 |
| WO | 2012/047954 | 4/2012 |
| WO | 2012/094643 | 7/2012 |
| WO | 2012/177945 | 12/2012 |
| WO | 2013/051928 | 4/2013 |
| WO | 2013088109 A1 | 6/2013 |
| WO | 2013/155010 | 10/2013 |
| WO | 2014/031610 | 2/2014 |
| WO | 2014/039461 | 3/2014 |
| WO | 2014/059178 | 4/2014 |
| WO | 2014/205365 | 12/2014 |
| WO | 2014197470 A1 | 12/2014 |
| WO | 2015/006571 | 1/2015 |
| WO | 2016077675 A1 | 5/2016 |
| WO | 2017/143270 | 8/2017 |
| WO | 2018/045130 | 3/2018 |
| WO | 2018/057776 | 3/2018 |

OTHER PUBLICATIONS

Bankhead, Charles, "IL-4 Antibody Tames Atopic Dermatitis", Medpage Today Article, https://www.medpagetoday.com/meetingcoverage/aad/37636, Mar. 3, 2013, 3 pages.

Clinical Trials, Study NCT01548404—"Study of REGN668 in Adult Patients With Extrinsic Moderate-to-Severe Atopic Dermatitis", first publication of clinical study protocol, Mar. 7, 2012, 7 pages.

Clinical Trials, Study NCT01548404—"Study of Dupilumab in Adult Patients with Extrinsic Moderate-to-severe Atopic Dermatitis", final publication of clinical study protocol, Aug. 27, 2015, 8 pages.

Clinical Trials, Study NCT00676884—"A Phase Study to Investigate the Effects of Repeated Administration of AeroDerm in Subjects with Atopic Dermatitis", Aeroderm first publication of clinical study protocol in TCS resistant moderate-to-severe AD, May 13, 2008, 6 pages.

Garriga, A., "71st Annual Meeting of the American Academy of Dermatology (AAAD) . . . Miami Beach, FL, Mar. 1-5, 2013", Drugs of the Future 2013, 38(4): 275-279, Apr. 2013, https://journals.prous.com/journals/servlet/xmlxls/pk_journals.xml_toc_pr?p_JournalID=28,p_IssueID=1186, 5 pages.

British Society for Allergy and Clinical Immunology (BSACI) Abstracts of the 2013 Annual Meeting (dated Jul. 8-10, 2013), Clinical & Experimental Allergy, 43, 1428-1472, Nov. 22, 2013, https://onlinelibrary.wiley.com/toc/13652222/2013/43/12, 45 pages.

Clinical Trials, Study NCT01639040—"Study to Assess the Safety of REGN668 (SAR231893) Administered Concomitantly with Topical Corticosteroids (TCS) in Patients with Moderate-to-severe Atopic Dermatitis (AD)", Concomitant treatment with TCS, Jul. 11, 2012, 6 pages.

Journal of Allergy & Clinical Immunology: Abstracts at conference; https://www.jacionline.org/issue/S0091-6749(13)X0013-2, Feb. 2013, 1 page.

Joost, T.H. Van, "Cyclosporin in atopical dermatitis: a multicentre placebo-controlled study", Journal of the American Academy of Dermatology, (1992), vol. 27, Issue 6, Part 1, pp. 922-928.

BSACI News Report confirming BSACI conference date of Jul. 8-10, 2013, 2 pages.

Clinical Trials Study No. NCT01312961—"Efficacy, Safety, and Tolerability of Dupilumab in Patients with Persistent Moderate to Severe Eosinophilic Asthma", In: ClinicalTrials.gov, A service of the U.S. National Institutes of Health, First Received: Mar. 11, 2011, 10 pages, Available from: https://clinicaltrials.gov/ct2/show/NCT01312961.

Dellon, Evan S. et al., "A Randomized, Double-Blind, Placebo-Controlled Trial of a Novel Recombinant, Humanized, Anti-Interleukin-13 Monoclonal Antibody (RPC4046) in Patients with Active Eosinophilic Esophagitis: Results of the HEROES Study", Oct. 14, 2016, retrieved from the Internet on Sep. 20, 2018 at: https://www.eventscribe.com/2016/ACG/QRcode.asp?Pres=178380, 3 pages.

Rothenberg, Marc E. et al., "Intravenous anti-IL-13 mAb QAX576 for the Treatment of eosinophilic esophagitis", Journal of Allergy and Clinical Immunology, vol. 135, No. 2, Feb. 1, 2015, pp. 500-507.

Hirano, Ikuo et al., "Dupilumab Efficacy and Safety in Adult Patients With Active Eosinophilic Esophagitis: a Randomized Double-Blind Placebo-Controlled Phase 2 Trial", Oct. 13, 2017, retrieved from the Internet on Sep. 20, 2018 at: http://files.shareholder.com/downloads/REGN/6138593856x0x959724/16AF93AE-DAF8-480A-8301-311C91E8FA41/Presentation.pdf, 20 pages.

Hirano, Ikuo et al., "Sa1113—Correlation Between Esophageal Distensibility and Objective Measures of Disease in Patients with Active Eosinophilic Esophagitis: A Post HOC Analysis of a Randomized, Placebo-Controlled, Phase 2 Dupilumab Trial", abstract, Gastroenterology, vol. 154, No. 6, May 1, 2018, 1 page.

Collins, Margaret H. et al., "Sa1151—Baseline Characteristics and Correlation Between Dysphagia and Disease Activity in Patients with Eosinophilic Esophagitis in a Randomized, Placebo-

(56) References Cited

OTHER PUBLICATIONS

Controlled, Phase 2 Dupilumab Trial", abstract, Gastroenterology, vol. 154, No. 6, May 1, 2016, 1 page.
Pesek, Robert D. et al., "Emerging drugs for eosinophilic esophagitis", Expert Opinion on Emerging Drugs, vol. 23, No. 2, Apr. 3, 2018, 12 pages.
Sanofi/Regeneron Press Release, "Sanofi and Regeneron Report Positive Results with Sarilumab in First Phase 3 Rheumatoid Arthritis Registration Trial", Paris, France and Tarrytown, NY, Nov. 22, 2013, 3 pages.
Almagro et al., "Humanization of antibodies", (2008) Frontiers in Bioscience 13:1619-1633.
Romaniuk, L.I., "Allergan-specific immunotherapy: mechanisms, methods and efficacy", Clinical Immunology, Allergology and Infectology, 2012, special issue, pp. 44-47. (with English translation of the cited portion).
Bagnasco, Diego et al., "A critical evaluation of Anti-IL-13 and Anti-IL-4 Strategies in Severe Asthma", Int. Arch Allergy Immunol 2016; 170: 122-131.
Durham, Andrew L. et al., "Targeted anti-inflammatory therapeutics in asthma and chronic obstructive lung disease", Airway Disease Section, Nat'l. Heart and Lung Institiute, Imperial Collge London, UK, published Aug. 12, 2015, 12 pages.
Kakinuma et al. (2001) J. Allergy Can. Immunol. 107(3):535-541 "Thymus and activation-regulated chemokine in atopic dertatitis: Serum thymus and activation-regulated chemokine level is closely related with disease activity".
Kakinuma et al. (2002) Clin. Exp. Immunol 127:270-273 "Serum macrophage-derived chemokine (MDC) levels are closely related with the disease activity of atopic dermatitis".
Kakkar et al. (2011) Pharmaceutical Research 28(10):2530-2542 "Population PK and IgE Pharmacodynamic Analysis of a Fully Human Monoclonal Antibody Against IL4 Receptor".
Katial (2009) Immunol Allergy Clin N Am 29:119-127 "Biomarkers for Nononcologic Gastrointestinal Disease".
Kelly and Liu (2014) World Allergy Organization Journal 7(S1):P8 "Poster 1013: IL-4R alpha antibody inhibits IgE production and airway remodeling in mouse model of house dust mite-induced cosinophilic asthma".
Kim et al. (2004) J Allergy Clin Immunol 114(6):1449-1455 "Rebound eosinophilia after treatment of hypereosinophilic syndrome and eosinophilic gastroenteritis with monoclonal anti-IL-5 antibody SCH55700".
Konikoff et al. (2006) Gastroenterology 131:1381-1391 "A Randomized, Double-Blind, Placebo-Controlled Trial of Fluticasone Propionate for Pediatric Eosinophilic Esophagitis".
Kopf et al. (1993) Letters to Nature 362:245-248 "Disruption of the murine IL-4 gene blocks Th2 cytokine responses".
Kostic et al. (2010) Clinical Immunology 135:S105-S106 "A Fully Human IL4Rα Antibody for Inhibition of IL-4/IL-13- driven TH2 Responses in Allergic Disease".
Kottyan et al. (2014) Nature Genetics "Genome-wide association analysis of eosinophilic esophagitis provides insight into the tissue specificity of this allergic disease".
Kulis et al. (2011) J. Allergy Clin Immunol 127:31-88 "Single-tree nut immunotherapy attenuates allergic reactions in mice with hypersensitivity to multiple tree nuts".
Leung et al. (2003) the New England Journal of Medicine 348:986-993 "Effect of Anti-IgE Therapy in Patients with Peanut Allergy".
Leung et al. (2004) the Journal of Clinical Investigation 113(5): 651-657 "New insights into atopic dermatitis".
Lezcano-Meza et al (2003) Allergy 58(10):1011-1017 "Interleukin (IL)-4 and to a lesser extent either IL-13 or interferon-gamma regulate the production of eotaxin-2/CCL24 in nasal polyps".
Liacouras et al. (2011) J Allergy Clin Immunol 128(1) "Eosinophilic esophagitis: Updated consensus recommendations for children and adults".
Lin et al (2007) Clinical Reviews in Allergy & Immunology 33(3):167-177 "Role of Bacterial Pathogens in Atopic Dermatitis".

Liu et al. (1999) Gene Therapy 6:1258-1266 "Hydrodynamics-based transfection in animals by systemic administration of plasmid DNA".
Lucendo and Sanchez-Cazalilla (2012) Expert Rev. Clin. Immunol. 8(8):733-745 "Adult versus pediatric eosinophilic esophagitis: important differences and similarities for the clinician to understand".
Ludmila and Xia (2014) World Allergy Organization Journal 7(1):P8 "Poster 1013: IL-4R alpha antibody inhibits IgE production and airway remodeling in mouse model of house dust mite-induced eosinophilic asthma".
Lwin et al. (2011) Modem Pathology 24:556-563 "Eosinophilic gastritis: histopathological characterization and quantification of the normal gastric eosinophil content".
MacCallum et al. (1996) J. Mol. Biol. 262:732-745 "Antibody-antigen Interactions: Contact Analysis and Binding Site Topography".
Maliszewski et al. (1994) Proc. Soc. Exp Bioi. Med. 206(3):233-237 "In vivo biological effects of recombinant soluble interleukin-4 receptor".
Mannon et al. (2012) GUT 61(12):1765-1773 "Interleukin 13 and its role in gut defence and inflammation".
Mariuzza et al. (1987) Ann. Rev. Biophys. Biophys. Che. 16:139-159 "The Structural Basis of Antigen-Antibody Recognition".
Masterson et al. (2011) Curr Opin Gastroenterol. 27(6):515-522 "Update on clinical and immunological features of eosinophilic gastrointestinal diseases".
Mishra and Rothenberg (2003) Gastroenterology 125:1419-1427 "Intratracheal IL-13 Induces Eosinophilic Esophagitis by an IL-5, Eotaxin-1, and STAT6-Dependent Mechanism".
Mishra et al. (2001) J Clin. Invest. 107:83-90 "An etiological role for aeroallergens and eosinophils in experimental esophagitis".
Mishra et al. (2002) The Journal of Immunology 168:2464-2469 "IL-5 Promotes Eosinophil Trafficking to the Esophagus".
Moldoveanu et al. (2009) Journal of Inflammation Research 2:1-11 "Inflammatory mechanisms in the lung".
Molfino et al. (2012) Clinical & Experimental Allergy 42(5):712-737 "Molecular and clinical rationale for therapeutic targeting of interleukin-5 and its receptor".
Morioka et al. (2009) British Journal of Dermatology 160(6):1172-1179 "IL-4/IL-13 antagonist DNA vaccination successfully suppresses Th2 type chronic dermatitis".
Müller et al. (1993) Journal of Immunology 150:5576-5584 "Th2 cells mediate IL-4-dependent local tissue inflammation".
Nadeau et al. (2011) J. Allergy Clin. Immunol 127(6) Letters to the Editor "Rapid oral desensitization in combination with ornalizurnab therapy in patients with cow's milk allergy".
Nguyen et al. (2011) Immunological Reviews 242(1):258-271 "Immune modulation for treatment of allergic disease".
Niederberger (2009) Immunology Letters 122:131-133 "Allergen-specific immunotherapy".
Niranjan et al. (2013) Immunology and Cell Biology pp. 1-8 "Pathogenesis of allergen-induced eosinophilic esophagitis is independent of interleukin (IL)-13".
Noel et al. (2004) The New England Journal of Medicine 351:940-941 "Eosinophilic Esophagitis".
Novartis (2013) QAX576 "A double blinded, randomized, placebo-controlled trial of intravenous QAX576 in the treatment of eosinophilic esophagitis".
Oh et al. (2010) Eur Respir Rev 19(115):46-54 "Investigational therapeutics targeting the IL-4/IL-13/STAT-6 pathway for the treatment of asthma".
Ohno et al. (1985) Proc. Natl. Acad. Sci. USA 82:2945-2949 "Antigen-binding specificities of antibodies are primarily determined by seven residues of VH".
Ong (2012) Expert Opinion on Emerging Drugs 17(2):129-133 "Editorial update on emerging treatments of atopic dermatitis".
Otani et al. (2013) Journal of Allergy and Clinical Immunology 131(6):1576-1582 "Anti-IL-5 therapy reduces mast cell and IL-9 cell numbers in pediatric patients with eosinophilic esophagititis".
Otulana et al. (2011) Am. J. Respir. Crit. Care Med. 183:A6179 "A Phase 2b Study of Inhaled Pitrakinra, an IL-4R/IL-13 Antagonist, Successfully Identified Responder Subpopulations of Patients with Uncontrolled Asthma".

(56) References Cited

OTHER PUBLICATIONS

Oyoshi et al. (2009) Advances in Immunology 102:135-226 "Cellular and Molecular Mechanisms in Atopic Dermatitis".
Peserico et al. (2008) British Journal of Dermatology 158:801-807 "Reduction of relapses of atopic dermatitis with methylprednisolone aceptonate cream twice weekly in addition to maintenance treatment with emollient: a multicentre, randomized; double-blind, controlled study".
Petry et al. (2012) Anais Brasileiro De Dermatologia 87(5):732-733 "Bacterial skin colonization and infections in patients with atopic dermatitis".
Prieto and Richter (2013) Curr Gastroenterol Rep 15:324 "Eosinophilic Esophagitis in Adults: an Update on Medical Management".
Prussin et al. (2009) J Allergy Clin Immunol. 124(6):1326-1332 "Eosinophilic gastrointestinal disease and peanut allergy are alternatively associated with IL-5+ and IL-5- TH2 responses".
Rafi et al. (2010) Allergy and Asthma Proceedings 31(1):76-83 "Effects of omalizumab in patients with food allergy".
Rayapudi et al. (2010) Journal of Leukocyte Biology 88 "Indoor insect allergens are potent inducers of experimental eosinophilic esophagitis in mice".
Whalley et al. (2004) British Journal of Dermatology 150:274-283 "A new instrument for assessing quality of life in atopic dermatitis: international deveioopment of the Quality of Life Index for Atopic Dermatitis (QoLIAD)".
Wilhelm and Stockinger (2011) Frontiers in Immunology 2(68) "Innate lymphoid cells and type 2 (Th2) mediated immune responses-pathogenic or beneficial?".
Wills-Karp and Finkelman (2008) Science Signaling 1(51) "Untangling the Complex Web of IL-4 and IL-13 Mediated Signaling Pathways".
Winkler et al. (2000) J. Immunol. 165(8):4505-4514 "Changing the Antigen Binding Specificity by Single Point Mutations of an Anti-p24 (HIV-1) Antibody".
Winter and Harris (1993) Immunology Today 14(6):243-246 "Humanized Antibodies".
Wo et al. (1999) Journal of Molecular Biology 294:151-162 "Humanization of a murine monoclonal antibody by simultaneous optimization of framework and CDR residues".
Yamanaka et al. (2011) Curr Probl Dermatol 41:80-92 "The Role of CytokinesiChemokines in the Pathogenesis of Atopic Dermatitis".
Yan and Shaffer (2006) World J Gastroenterol 12(15):2328-2334 "Eosinophilic esophagitis: A newly established cause of dysphagia".
Zuo et al. (2010) Journal of Immunology 185:660-669 "IL-13 Induces Esophageal Remodeling and Gene Expression by an Eosinophil-Independent, IL-13R{alpha}-Inhibited Pathway".
Zurawski et al. (1995) J. Bioi. Chem. Am. Society of Biolochemical Biologists 270(23):13869-13878 "The primary binding subunit of the human Interleukin-4 receptor is also a component of the Interleukin-13 receptor".
Official Action from Russian Federation for RU Appl. No. 2016104400, dated Oct. 6, 2017, translation.
Receptos, Inc. 2013 Annual Report.
Ring et al. (2012) J. Eur. Acad. Dermatol. Venereol. 26(8):1045-1060 "Guidelines for treatement of atopic eczema (atopic dermatitis) Part 1".
Roitt et al. (2001) Mosby—Harcourt Publishers Limited, Immunology—Sixth Edition "Antigen Presentation" pp. 110-111.
Roll et al. (2006) J. Investig Allergol Clin Immunol 16(2):79-85 "Safety of specific immunotherapy using a four-hour ultra-rush induction scheme in bee and wasp allergy".
Rothenberg (2004) J Allergy Clin Immunol 113(1):11-28 "Eosinophilic gastrointestinal disorders (EGID)".
Rothenberg (2009) Gastroenterology 137:1238-1249 "Biology and Treatment of Eosinophilic Esophagitis".
Rudikoff et al. (1982) Proc. Natl. Acad. Sci. 79:1979-1983 "Single amino acid substitution altering antigen-binding specificity".
Saeki (2009) Advances in Medicine, Special Issue 228(1):75-79 "Guideline for management of atopic dermatis by the Japanese Dermatological Association".

Simpson, Eric L. et al., "Dupilumab therapy provides clinically meaningful improvement in patient-reported outcomes (PROs): A phase llb, randomized, placebo-controlled, clinical trial in adult patients with moderate to severe atopic dermatitis (AD)", Journal of the American Academy of Dermatology, Mosby, Inc., US, vol. 75, No. 3, Jun. 4, 2016 (Jun. 4, 2016.
Simpson, Eric L. et al., "Patient burden of moderate to severe atopic dermatitis (AD): Insights from a phase 2b clinical trial of dupilumab in adults," Journal of the American Academy of Dermatology, Mosby, Inc., US, vol. 74, No. 3, Jan. 14, 2016.
Tsianakas, Athanasios et al., "Dupilumab: A Milestone in the Treatment of Atopic Dermatitis," The Lancet, The Lancet Publishing Group, GB vol. 387, No. 10013, Oct. 8, 2015.
Thaci, Diamant et al.: "Efficacy and Safety of Dupilumab in Adults with Moderate-to-Severe Atopic Dermatitis Inadequately Controlled by Topical Treatments: A Randomised, placebo-Controlled, dose-ranging phase 2b trial," The Lancet, The Lancet Publishing Group, GB, vol. 387, No. 10013, Oct. 8, 2015.
Ivashkin, V. I., et al., "Eosinophilic esophagitis," a textbook for physians, Moscow, "AISPI RAS" JSC, Feb. 14, 2013, pp. 13-21, 57-62; No English Translation—(cited in Russian Office Action RU Appl. No. 2016104400).
Sampson et al. (2011) J. Allergy Clin Immunol. 127(5) Letters to the Editor, "A phase II, randomized, double-blind, parallel-group, placebo controlled oral food challenge trial of Xolair (omalizumab) in peanut allergy".
Sanofi and Regeneron Report Positive Proof-of-Concept Data for Dupilumab, an IL-4R alpha Antibody, in Atopic Dermatitis, 71st Annual Meeting of the American Academy of Dermatology (2013) http://files.shareholder.com/downloads/REGN/2689212012x0x640531/794a7e54-6904-416b-ba38-a4ccc1726852/REGN_News_2013_3_2_General_Releases.pdf.
Sanofi with Regeneron Pharmaceuticals "An Evaluation of Dupilumab in Patients with Nasal Polyposis and Chronic Symptoms of Sinusitis" Trial in Progress, Jun. 2014. ClinicalTrials.gov Identifier: NCT01920893. Retrieved from the Internet URL: http://clinicaltrials.govishow/NCT01920893 Accessed on Sep. 29, 2014.
Sato et al. (1993) J. Immunol. 150(7):2717-2723 "Recombinant soluble murine IL-4 receptor can inhibit or enhance IgE responses in vivo".
Scavuzzo et al. (2005) Biomedicine & Pharmacotherapy 59(6):323-9 "Inflammatory mediators and eosinophilia in atopic and non-atopic patients with nasal polyposis".
Schmidt-Weber (2012) Chem Immunol Allergy 96:120-125 "Anti-IL-4 as a New Strategy in Allergy".
Schmitt et al. (2007) J. of Allergy and Clinical Immunology 120(6):1389-1398 "What are the best outcome measurements for atopic eczema? A systematic review".
Schneider et al. (2013) J. Allergy Clin Immunol 132(6):1368-1374 "A pilot study of omalizumab to facilitate rapid oral desensitization in high-risk peanut-allergic patients".
Sekiya et al. (2002) Allergy 57:173-177 "Increased levels of a TH2-type CC chemokine thymus and activation-regulated chemokine (TARC) in serum and induced sputumm of asthmatics".
Slager et al. (2012) Journal of Allergy, Asthma and Immunology 130(2):516-522.e4 "IL-4 Receptor Polymorphisms Predict Reduction in Asthma Exacerbations During Response to an Anti IL-4 Receptor Antagonist".
Spirin (1986) Vysshaya shkola, Moscow, pp. 17-23 "Molecular Biology ribosome structure and protein biosynthesis," original Russian article and English language translation of same provided by foreign associate handling local prosecution of Russian application No. 2011120194.
Stein et al. (2006) J Allergy Clin Immunol 118(6):1312-1319 "Anti-IL-5 (mepolizumab) therapy for eosinophilic esophagitis".
Steinke and Borish (2001) Respiratory Research 2(2): 1-5 "Th2 cytokines and asthma interleukin-4: its role in the pathogenesis of asthma, and targeting it for asthma treatment with interleukin-4 receptor antagonists".
Stone et al. (2008) Clinical & Experimental Allergy 38( 12): 1858-1865 "I mmunomodulatory therapy of eosinophil-associated gastrointestinal diseases".

(56) References Cited

OTHER PUBLICATIONS

Strauman (2009) Immunol Allergy Clin N Am 29:11-18 "Clinical Evaluation of the Adult who has Eosinophilic Esophagitis".
Straumann (2005) J Allergy Clin I mmunol 115(2):418-419 "Eosinophilic esophagitis: Escalating epidemiology?".
Straumann et al. (2001) J Allergy Clin Immunol 108(6):954-961 "Idiopathic eosinophilic esophagitis is associated with a TH2-type allergic inflammatory response".
Straumann et al. (2009) Gut "Anti-interleukin-5 antibody treatment (mepolizumab) in active eosinophilic oesophagitis: a randomized, placebo-controlled, double-blind trial".
Tazawa et al. (2004) Arch Dermatol Res 295:459-464 "Relative importance of IL-4 and IL-13 in lesion al skin of atopic dermatitis".
Tepper et al. (1990) Cell 52:457-467 "IL-4 linduces Allergic-like Inflammatory Disease and alters T Cell Development in Transgenic Mice".
Tomkinson et al. (2001) J. Immunol 166:5792-5800 "A Murine IL-4 Receptor Antagonist that Inhibits IL-4-and IL-13-induced Responses Prevents Antigen-Induced Airway Eosinophilia and Airway Hyper-responsiveness".
Vajdos et al. (2002) Journal of Molecular Biology 320(2):415-428 "Comprehensive functional maps of the antigen-binding site of an anti-ErbB2 antibody obtained with shotgun scanning mutagenesis".
Veerappan et al. (2009) Clinical Gastroenterology and Hepatology 7:420-426 "Prevalence of Eosinophilic Esophagitis in an Adult Population Undergoing Upper Endoscopy: A Prospective Study".
Vestergaard et al. (2000) The Journal of Investigative Dermatology 115(4):640-646 "A Th2 Chemokine, TARC, Produced by Keratinocytes May Recruit CLA+CCR4+ Lymphocytes into Lesional Atopic Dermatitis Skin".
Virchow et al. (1994) Lung 172:313-334 "Cellular and immunological markers of allergic and intrinsic bronchial asthma".
Walker et al. (1993) Clinical and Experimental Allergy 23:145-153 "Atopic dermatitis: correlation of peripheral blood T cell activation, eosinophilia and serum factors with clinical severity".
Wang and Liu (2008) Current Opinion in Immunology 20:697-702 "The IL-17 cytokine family and their role in allergic inflammation".
Wark et al. (2006) Advanced Drug Delivery Reviews 58:657-670 "Latest technologies for the enhancement of antibody affinity".
Watson et al. (2011) Allergy, Asthma & Clinical Immunology 7:S4 "Atopic dermatitis".
Weihrauch et al. (2005) Cancer Research 65:5516-5519 "Elevated Serum Levels of CC Thymus and Activation-Related Chemokine (TARC) in Primary Hodgkin's Disease: Potential for a Prognostic Factor".
Weinbrand-Goichberg et al. (2013) Immunol Res "Eosinophilic esophagitis: an immune-mediated esophageal disease".
Wenzel et al. (2007) Lancet 370:1422-1431 "Effect of an interleukin-4 variant on late phase asthmatic response to allergen challenge in asthmatic patients: results of two phase 2a studies".
Wenzel et al. (2010) European Respiratory Society, Annual Congress "ERS—Programme" pp. 3980.
Wenzel et al. (2013) New England Journal of Medicine 368(26):2455-2466 "Dupilumab in Persistent Asthma with Elevated Eosinophil Levels".
Wershil (2009) Immunol Allergy Clin N Am 29:189-195 "Exploring the Role of Mast Cells in Eosinophilic Esophagitis".
Kopp, M.V. et al., "Combination of omalizumab and specific immunotherapy is superior to immunotherapy in patients with seasonal allergic rhinoconjunctivitis and co-morbid seasonal allergic asthma", Clinical and Experimental Allergy, vol. 39, No. 2, pp. 271-279, published on Jan. 22, 2009.
Cortes, J. R, et al., Proton pump inhibitors inhibit IL-4 and IL-13 signaling stat6 activation, European Journal of Ummunology, (Sep. 2009) vol. 39, Supp.
Ivashkin, V. T., et al., "Eosinophilic esophagitis: literature review and description of own survey," RJGHC, 2012, vol. 22, 1, pp. 71-81.
Ivashkin, V. I., et al., "Eosinophilic esophagitis," a textbook for physicians, Moscow, "AISPI RAS" JSC, Feb. 14, 2013, pp. 13-21, 57-62 No English translation. (cited in Russian Office Action for RU Appl. No. 2016104400).
Assa'ad, Amal, "What is new in the Treatment of Eosinophilic Eosophagitis?" Clinical and Translational Allergy 2011 (Suppl 1):S69, doi:10.1186/2045-7022-1-S1-S69.
Bieber, T., et al., "Atopic dermatitis: a candidate for disease-modifying strategy," Allergy 67 (Apr. 12, 2012) 969-975.
Sanofi, "Positive Phase 2a Results of Dupilumab in Asthma in the New England Journal of Medicine," May 21, 2013, Regeneron Pharmaceuticals, Inc.
Wang, et al., "Peanut-induced intestinal allergy is mediated through a mast cell-IgE-FceRI-IL-13 Pathway," Journal of Allergy and Clinical Immunology, 2010, vol. 126, No. 2, 306-316, e1-e12.
Nadeau, et al., "Oral Immunotherapy and Anti-IgE Antibody-Adjunctive Treatment for Food Allergy," Immunology and Allergy clinics of North America, 2012, vol. 32, No. 1, 111-133.
Mathias, et al., IgE-mediated systemic anaphylaxs and impaired tolerance to food antigens in mice with enhanced IL-4 receptor signaling, Journal of Allergy and Clinical Immunology, 2011, vol. 127, No. 3, 795-805, e1-e6.
Burton, et al., "Direct effects of IL-4 on mast cells drive their intestinal expansion and increase susceptibility to anaphylaxis in a murine model of food allergy," Mucosal Immunology, Nov. 14, 2012, doi:10.1038/mi.2012.112.
Akiyama, et al., A Study on Indoor Allergens Measured in Home Environments of Adult-Asthmatic Patients, Study No. 9620, 1-10.
Terui, et al., "Learning from Fungus Allergy in Atopic Dermatitis Patients," Japan J. Med. Mycol, 2000, vol. 41, No. 3, 157-160.
Wong, et al., "Guidelines for the management of atopic dermatitis (eczema) for pharmacists," CPJ/RPC, Sep./Oct. 2017, vol. 150, No. 5.
Highlights of Prescribing Information, DUPIXENT (dupilumab) injection, for subcutaneous use Initial U.S. Approval: 2017, U.S. Food and Drug Administration (FDA), Revised Mar. 2017.
Hong, Judith, et al., "Management of Itch in Atopic Dermatitis," Seminars in cutaneous Medicine and Surgery, vol. 30, No. 2, May 14, 2011, pp. 71-86 XP028240445.
Paton, D. M., "Dupilumab: human monoclonal antibody against IL-4Ralpha for moderate to severe atopic dermatitis," Drugs Today, vol. 53, No. 9, Sep. 1, 2017, pp. 477-487, XP055465888.
Akiyama, et al., A Study on Indoor Allergens Measured in Home Environments of Adult-Asthmatic Patients, Housing Research Foundation, Research Annual Report, 1997, No. 24, Study No. 9620, 1-10.
Abonia et al. (2013) Journal of Allergy Clin Immunol "High prevalence of eosinophilic esophagitis in patients with inherited connective tissue disorders".
Aceves et al. (2009)Immunol Allergy Clin N Am 29:197-211 "Relationships Between Eosinophilic Inflammation, Tissue Remodeling, and Fibrosis in Eosinophilic Esophagitis".
Arron et al. (2009) Am. J. Respir. Crit. Care Med. Online Abstracts Issue. 2009, B21 Airway Inflammation: New Information about Mediators and Biomarkers/Poster Discussion/Monday, May 18, 2009 "Peripheral Biomarkers of an IL-13 induced Bronchial Epithelial Gene Signature in Asthma".
Assa'ad et al. (2011) Gastroenterology 141:1593-1604 "An Antibody Against IL-5 Reduces Nos. Of Esophageal Intraepithelial Eosinophils in Children with Eosinophilic Esophagitis".
Bachert et al. (2005) Drugs 65(11):1537-1552 "Pharmacological management of nasal polyposis".
Balint and Larrick (1993) Gene 137:109-118 "Antibody engineering by parsimonious mutagenesis".
Barnes (2008) The Journal of Clinical Investigation 118(11):3546-3556 "The cytokine network in asthma and chronic obstructive pulmonary disease".
Bateman et al. (2004) Am. J. Respir. Crit. Care Med. 170:836-844 "Can guideline-defined asthma control be achieved?".
Beck et al. (2014) New England Journal of Medicine 371(2): 130-139 "Dupilumab treatment in adults with moderate-to-severe atopic dermatitis".

(56) References Cited

OTHER PUBLICATIONS

Beyer et al. (2002) Journal of Allergy Clin Immunol 109(4):707-713 "Human milk-specific mucosal lymphocytes of the gastrointestinal tract display a TH2 cytokine profile".
Bhardwa and Ghaffari (2012) Ann Allergy Asthma Immunol 109:155-159 "Biomarkers for eosinophilic esophagitis: a review".
Blanchard and Rothenberg (2009) Immunol Allergy Clin N Am 29:141-148 "Chemotactic Factors Associated with Eosinophilic Gastrointestinal Diseases".
Blanchard et al. (2005) Clin Exp Allergy 35:1096-1103 "Inhibition of human interleukin-13-induced respiratory and oesophageal inflammation by anti-human-interleukin-13 antibody (CAT-354)".
Blanchard et al. (2006) the Journal of Clinical Investigation 116(2) "Eotaxin-3 and a uniquely conserved gene-expression profile in eosinophilic esophagitis".
Blanchard et al. (2007) Journal of Allergy Clin Immunol 120(6) "IL-13 involvement in eosinophilic esophagitis: Transcriptome analysis and reversibility with glucocorticoids".
Blanchard et al. (2010) The Journal of Immunology "Coordinate Interaction between IL-13 and Epithelial Differentiation Cluster Genes in Eosinophilic Esophagitis".
Blanchard et al. (2011) J Allergy Clin Immunol 127(1):208-217 "A striking local esophageal cytokine expression profile in eosinophilic esophagitis".
Brown-Whitehorn and Spergel (2010) Expert Rev Clin Immunol. 6:1:101-115 "The link between allergies and eosinophilic esophagitis: implications for management strategies".
Burmeister-Getz et al. (2009) J. Clin. Pharmacol. 49:1025-1036 "Human pharmacokinetics/pharmacodynamics of an interleukin-4 and interleukin-13 dual antagonist in asthma".
Caldas et al. (2003) Molecular Immunology 39:941-952 "Humanization of the anti-CD18 antibody 6.7: an unexpected effect of a framework residue in binding to antigen".
Carter (2006) The Journal of Immunology 6:343-357 "Potent Antibody Therapeutics by Design".
Gasset et al. (2003) Biochemical and Biophysical Research Communication 307:198-205 "A peptide mimetic of an anti-CD4 monoclonal antibody by rational design".
Chehade and Sampson (2009) Imrnunol Allergy Clin N Am 29:149-158 "The Role of Lymphocytes in Eosinophilic Gastrointestinal Disorders".
Cheng et al. (2012) Am J Physiol Gastrointest Liver Physiol 303:G1175-G1187 "Tissue remodeling in eosinophilic esophagitis".
Chien et al (1989) Proc. Natl. Acad. Sci. 86 5532-5536 "Significant structural and functional change of an antigen-binding site by a distant amino acid substitution: Proposal of a structural mechanism".
Corren et al. (2010) American Journal of Respiratory and Critical Care Medicine 181(8):788-796 "A Randomized, Controlled, Phase 2 Study of AMG 317, an IL-4R Antagonist, in Patients with Asthma".
Davies et al. (1996) Immunotechnol. 2(3):169-179 "Affinity improvement of single antibody VH domains: residues in all three hypervariable regions effect antigen binding".
Davis (2004) Seminars in Immunology 16:239-243 "The evolutionary and structural 'logic' of antigen receptor diversity".
De Pascalis et al. (2002) Journal of Immunology 169(6):3076-3084 "Grafting of "Abbreviated" Complementarity-Determining Regions Containing Specificity-Determining Residues Essential for Ligand Contact to Engineer a Less Immunogenic Humanized Monoclonal Antibody".
Dellon (2013) Dig Dis Sci "The Pathogenesis of Eosinophilic Esophagitis: Beyond the Eosinophil".
Desreumaux et al. (1996) Gastroenterology 110:768-774 "Interleukin 3, Granulocyte-Macrophage Colony-Stimulating Factor, and Interleukin 5 in Eosinophilic Gastroenteritis".
Fillon et al. (2009) Immunol Allergy Clin N Am 29:171-178 "Epithelial Function in Eosinophilic Gastrointestinal Diseases".
Foote and Winter (1992) J. Mol. Biol. 224:487-499 "Antibody Framework Residues Affecting the Conformation of the Hypervariable Loops".
Foroughi et al. (2007) J Allergy Clin Immunol 120(3):594-601 "Anti-IgE Treatment of Eosinophil Associated Gastrointestinal Disorders".
Franciosi and Liacouras (2009) Immunol Allergy Clin N Am 29:19-27 "Eosinophilic Esophagitis".
Gavett et al. (1997) The American Physiological Society 272(16):L253-L261 "Interleukin-4 receptor blockade prevents airway responses induced by antigen challenge in mice".
Gevaert et al. (2006) Journal of Allergy and Clinical Immunology 118(5):1133-1141 "Nasal IL-5 levels determine the response to anti—IL-5 treatment in patients with nasal polyps".
Giusti et al. (1987) Proc. Natl. Acad. Sci. 84:2926-2930 "Somatic diversification of S107 from an antiphosphocholine to anti-DNA autoantibody is due to a single base change in its heavy chain variable region".
Groves et al. (2007) AERODERM in AD Poster at St. John's Institute of Dermatology "Inhibition of IL-4 and IL-13 with an IL-4 mutein (Aeroderm) protects against flares in atopic eczema".
Grunewald et al. (1998) The Journal of Immunology 160(8):4004-4009 "An Antagonistic IL-4 Mutant Prevents Type I Allergy in the Mouse: Inhibition of the IL-4/IL-13 Receptor System completely Abrogates Humoral Immune Response to Allergen and Development of Allergic Symptoms in Vivo".
Gussow and Seemann (1991) Methods in Enzymology 203:99-121 "Humanization of Monoclonal Antibodies".
Hijnen et al (2004) J. Allergy Clin. Immunology 113(2): 334-340 "Serum thymus and activation-regulated chemokine (TARC) and cutaneous T Cell-attracting chemokine (CTACK) levels in allergic diseases: TARC and CTACK are disease-specific markers for atopic dermatitis".
Holm et al. (2007) Molecular Immunology 44:1075-1084 "Functional mapping and single chain construction of the anti-cytokeratin 8 monoclonal antibody TS1".
Holt et al. (2003) Trends in Biotechnology 21(11):484-490 "Domain antibodies: proteins for therapy".
Hopkins et al. (2007) Otolaryngology-Head and Neck Surgery 137(4):555-561 "The Lund-Mackay staging system for chronic rhinosinusitis: How is it used and what does it predict?".
Hopkins (2009) Clinical Otolaryngology 34(5):447-454 "Psychometric validity of the 22-item Sinonasal Outcome Test".
Jahnz-Rozyk et al. (2005) Allergy 60:685-688 "Serum thymus and activation-regulated chemokine, macrophage-derived chemokine and eotaxin as marker of severity of atopic dermatitis".
Junttila et al. (2008) J. Exp. Med. 205(11):2595-2608 "Tuning sensitivity to IL-4 and IL-13: differential expression of IL-4Rα, IL-13Rα1, and Yc regulates relative cytokine sensitivity".
Jyonouchi et al. (2013) Basic Mechanisms in Allergic Disease "Invariant Natural Killer T cells in children with Eosinophilic Esophagitis".
Kagami et al. (2003) Clin. Exp. Immunology 134:309-313 "Significant elevation of serum levels of eotaxin-3/CCL26, but not of eotaxin-2/CCL24, in pateints with atopic dermatitis: serum eotaxin-3/CCL26 levels reflect the disease activity of atopic dermatitis".
Martel, Britta C., et al., "Translational animal Models of Atopic Dermatitis for Preclinical Studies," Yale Journal of Biology and Medicine 90 (2017), pp. 389-402.
Silverberg J.I., et al., "Dupilumab treatment induces rapid clinical improvement of itch in patients with moderate-to-severe atopic dermatitis" Paper presented at: American Academy of Dermatology—76th Annual Meeting; Feb. 16-20, 2018; San Diego, CA, USA.
Silverberg J.I., et al., P481, "Dupilumab treatment rapidly improves itch in patients with moderate-to-severe atopic dermatitis" An Allergy Asthma Immunol. 2017;119(suppl 5):S95.
Hamilton, Jennifer D., et al., "Drug evaluation review: Dupilumab in atopic dermatitis," Immunotherapy (2015) 7(10), 1043-1058.
Blauvelt, Andrew, et al., "Long-term management of moderate-to-severe atopic dermatitis with dupilumab and concomitant topical corticosteroids (Liberty Ad Chronos): a 1-year, randomised, double-

(56) References Cited

OTHER PUBLICATIONS blinded, placebo-controlled, phase 3 trial," www.thelancet.com, published online May 4, 2016, http://dx.doi.org/10.1016/S0140-6736(17)31191-1.

Simpson, E.L., et al., "Two Phase 3 Trials of Dupilumab versus Placebo in Atopic Dermatitis," The New England Journal of Medicine, Oct. 1, 2016, DOI: 10.1056/NEJMoa1610020.

Oetjen, Landon K., et al., "Sensory Neurons Co-opt Classical Immune Signaling Pathways to Mediate Chronic Itch," Sep. 21, 2017, Cell 171, 217-228.

Vakharia, Paras P. et al., "Monoclonal Antibodies for Atopic Dermatitis: Progress and Potential", BioDrugs (2017) 31:409-422.

Ul-Haq, Zaheer et al., "Interleukin-4 receptor signaling and its binding mechanism: A therapeutic insight from inhibitors tool box", Cytokine & Growth Factor Review 32 (2016) 3-15.

Mueller, Thomas D. et al., "Structure, binding, and antagonists in the IL-4/IL-13 receptor system", Biochimica et Biophysica Acta (2002) 237-250.

Regeneron 2011 Annual Report (Apr. 2011), 12 pages.

ClinicalTrials.gov archive, History of Changes for Study: NCT01548404, "Study of Dupilumab in Adult Patients with Extrinsic Moderate-to-Severe Atopic Dermatitis", (Apr. 19, 2012), 7 pages.

ClinicalTrials.gov archive, History of Changes for Study: NCT01259323, "Sequential Ascending Dose Study to Assess the Safety and Tolerability of REGN668 (SAR231893) in Patients With Atopic Dermatitis", (May 31, 2012), 6 pages.

Regeneron: "Highlights of Prescribing Information See 17 for Patient Counseling Information and FDA-approved patient labeling. Revised: Mar. 2017 Full Prescribing Information: Contents 1 Indications and Usage 2 Dosage and Administration 2.1 Dosage 2.2 Important Administration Instructions 2.3 Preparation for Use", (Apr. 7, 2017), XP055534130, Retrieved from the Internet: URL: https://web.archive.org/web/20170407151633if_/https://www.regeneron.com/sites/default/files/Dupixent_FPI.pdf, 4 pages.

Huang, Evie et al: "Severe Atopic Dermatitis in Children", Current Allergy and Asthma Reports, Current Science, US, vol. 18, No. 6, May 10, 2018, pp. 1-8.

Akinlade, B. et al: "Conjunctivitis in dupilumab clinical trials", British Journal of Dermatology, (Mar. 9, 2019), pp. 1-15.

Regeneron: "Dupixent: Highlights of Prescribing Information", (Mar. 1, 2019), pp. 1-8, XP55610296, Retrieved from the Internet: URL: https://dlegnxy4jx1q3f.cloudfront.net/Regeneron/Dupixent_FPI.pdf, 8 pgs.

Paller et al: "Early and sustained, clinically meaningful responses with dupilumab treatment in a phase 3 trial in adolescents with moderate-to-severe atopic dermatitis", Pediatric Dermatology, vol. 36, No. Suppl. 1, (Apr. 29, 2019), p. S4.

Database Embase [Online], Elsevier Science Publishers, Amsterdam,NL; (May 1, 2019), Cork M. J: "605 Efficacy and safety of dupilumab in adolescent patients with moderate-to-severe atopic dermatitis", XP002793331, Database accession No. EMB-002001809007 abstract, 3 pages.

Database Embase [Online], Elsevier Science Publishers, Amsterdam,NL; (May 1, 2019), Paller, A.S.: "621 Dupilumab in adolescents with moderate-to-severe atopic dermatitis and a history of inadequate response, or intolerance to cyclosporine: subgroup analysis from a pivotal 16-week trial", XP002793332, Database accession No. EMB-002001808313, Abstract, 2 pages.

\* cited by examiner

Peanut Allergy Mouse Model
(two dose administration)

*p<0.05 compared to isotype control

Peanut Allergy Mouse Model
(single administration on Day13)

Total IgE Levels

METHODS FOR TREATING ALLERGY AND ENHANCING ALLERGEN-SPECIFIC IMMUNOTHERAPY BY ADMINISTERING AN ANTIBODY TO IL-4 RECEPTOR

CROSS-REFERENCE TO RELATED APPLICATIONS

This application is a Divisional of U.S. application Ser. No. 14/294,544, filed on Jun. 3, 2014, which claims the benefit under 35 U.S.C. § 119(e) of U.S. provisional application No. 61/830,919, filed on Jun. 4, 2013, the disclosures of each herein incorporated by reference in their entireties.

SEQUENCE STATEMENT

The instant application contains a Sequence Listing, which has been submitted electronically in ASCII format and is hereby incorporated by reference in its entirety. Said ASCII copy, created on Dec. 6, 2017, is named SequenceList_12_D2.TXT and is 8 kilobytes in size.

FIELD OF THE INVENTION

The present invention relates to the use of interleukin-4 receptor inhibitors to treat or prevent allergic reactions and to improve the efficacy and/or safety of allergen-specific immunotherapy regimens.

BACKGROUND

Allergies and allergic diseases are serious medical conditions with consequences ranging from non-life threatening responses that resolve over time to life threatening effects such as anaphylaxis. Allergic reactions can result from contact or exposure to a variety of products such as certain food items, insect venom, plant-derived material (e.g., pollen), chemicals, drugs/medications, and animal dander. Current treatment options for allergies include avoidance, pharmacological symptom treatment and prophylaxis using allergen-specific immunotherapies (SIT). Unfortunately, these current treatment strategies are often inadequate, costly, impractical or involve significant risk. For example, avoidance of allergen is not always possible and can negatively impact on patient and caregiver quality of life. Immunotherapeutic approaches, on the other hand, involve deliberate administration of allergen to susceptible individuals and is therefore inherently risky with the potential for unwanted severe allergic reactions or anaphylaxis. Accordingly, an unmet need exists in the art for novel therapeutic approaches that prevent or treat allergic responses and improve the safety and/or efficacy of immunotherapeutic treatment strategies.

BRIEF SUMMARY OF THE INVENTION

According to one aspect of the present invention, methods are provided for treating, preventing or reducing the severity of an allergic reaction in a subject. The methods according to this aspect of the invention comprise administering a therapeutically effective amount of a pharmaceutical composition comprising an interleukin-4 receptor (IL-4R) antagonist to a subject in need thereof. The pharmaceutical composition comprising the IL-4R antagonist may be administered to the subject either before, during or after allergen exposure or manifestation of an allergic symptom.

According to another aspect of the present invention, methods are provided for enhancing the efficacy and/or safety of an allergen-specific immunotherapy (SIT) regimen. The methods according to this aspect of the invention comprise administering a therapeutically effective amount of a pharmaceutical composition comprising an IL-4R antagonist to a subject in combination with the SIT regimen. According to certain embodiments of this aspect of the invention, the pharmaceutical composition comprising the IL-4R antagonist is administered to the subject either before the commencement of the SIT regimen or during the course of the SIT regimen. For example, the pharmaceutical composition comprising the IL-4R antagonist may be administered during the up-dosing phase of the SIT regimen and/or during the maintenance phase of the SIT regimen.

According to another aspect of the present invention, methods are provided for reducing total serum IgE levels in a subject who has been exposed to an allergen. The methods according to this aspect of the invention comprise administering a pharmaceutical composition comprising an IL-4R antagonist to the subject in an amount sufficient to reduce or abrogate IgE production or to reduce or eliminate serum IgE levels in the subject.

In various embodiments, the pharmaceutical composition comprising the IL-4R antagonist is administered orally, sub-cutaneously, epi-cutaneously or intravenously to a subject in need thereof.

Exemplary IL-4R antagonists that can be used in the context of the methods of the present invention include, e.g., small molecule chemical inhibitors of IL-4R or its ligands (IL-4 and/or IL-13), or biological agents that target IL-4R or its ligands. According to certain embodiments, the IL-4R antagonist is an antigen-binding protein that binds the IL-4Rα chain and blocks signaling by IL-4, IL-13, or both IL-4 and IL-13. One such type of antigen-binding protein that can be used in the context of the methods of the present invention is an anti-IL-4Rα antibody such as dupilumab.

Other embodiments of the present invention will become apparent from a review of the ensuing detailed description.

DETAILED DESCRIPTION

Figure 1:
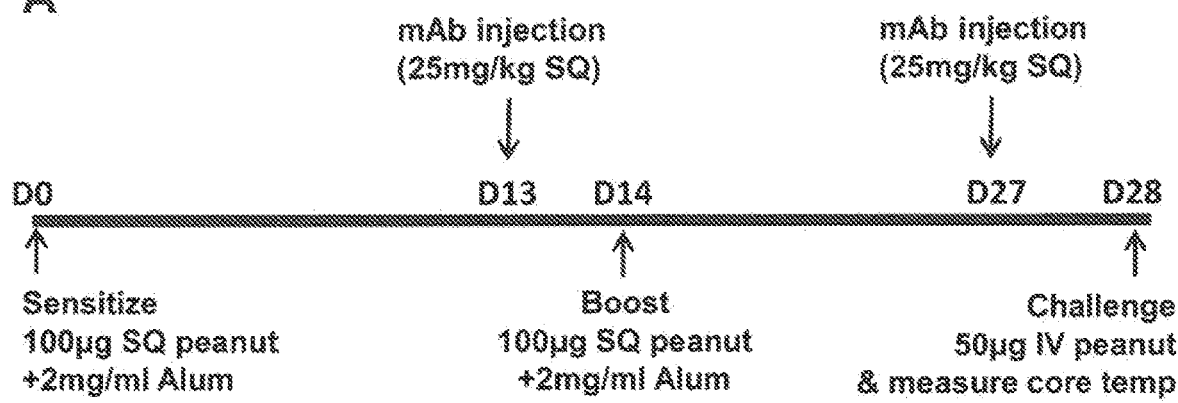
FIG. 1, Panel A depicts the time course of a peanut allergy mouse model in which two doses of an anti-IL-4Rα antibody were administered to the mice. Panel B shows the extent of anaphylaxis in three groups of experimental mice, assessed in terms of core temperature decrease over time following IV peanut extract challenge. Mice receiving no antibody are designated with grey filled circles; mice receiving anti-IL-4Rα antibody are designated with black filled squares; mice receiving isotype control antibody are designated with open squares.
Figure 1:
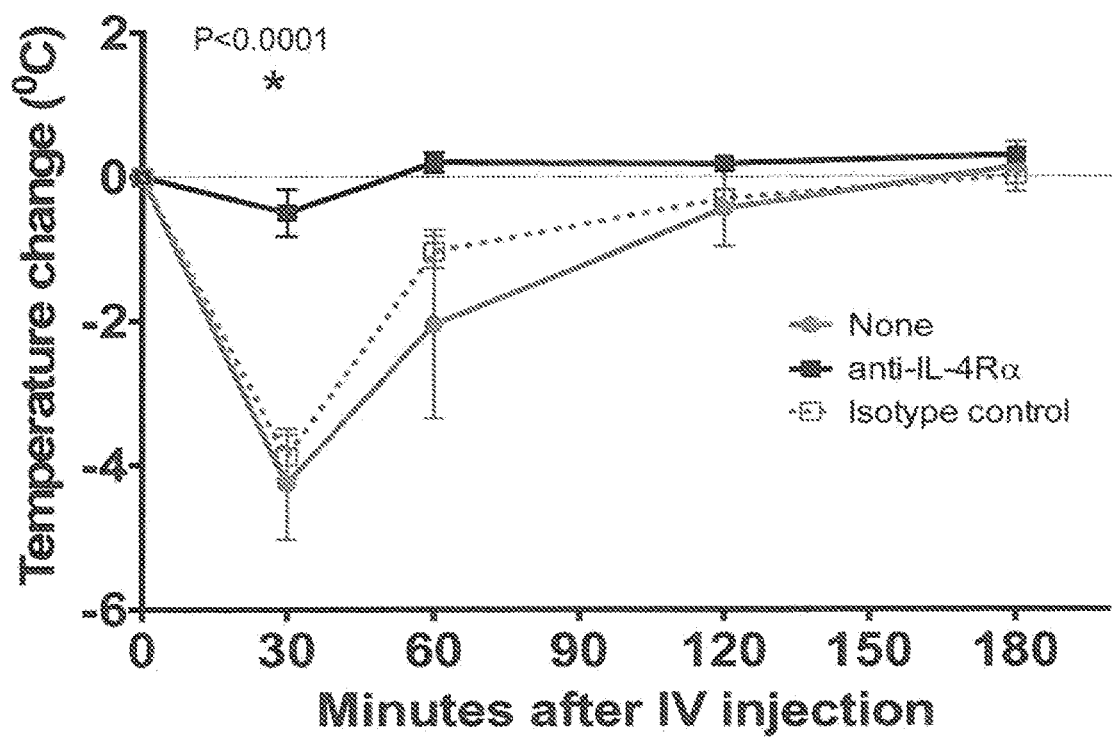

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Treating, Preventing or Reducing the Severity of Allergic Reactions

The present invention includes methods for treating, preventing or reducing the severity of an allergic reaction in a subject. The methods, according to this aspect of the invention, comprise administering a therapeutically effective amount of a pharmaceutical composition comprising an interleukin-4 receptor (IL-4R) antagonist to a subject in need thereof. As used herein, the terms "treat", "treating", or the like, mean to alleviate symptoms, eliminate the causation of symptoms either on a temporary or permanent basis, or to prevent or slow the appearance of symptoms of an allergic reaction. As used herein, the term "a subject in need thereof" means any human or non-human animal who: (a) is prone to allergic reactions or responses when exposed to one or more allergens; (b) has previously exhibited an allergic response or reaction to one or more allergens; (c) has a known history of allergies; and/or (d) exhibits a sign or symptom of an allergic response or anaphylaxis.

The present invention also includes methods for reducing total serum IgE levels in a subject who has been exposed to an allergen. The methods according to this aspect of the invention comprise administering a pharmaceutical composition comprising an interleukin-4 receptor (IL-4R) antagonist to the subject in an amount sufficient to reduce or abrogate IgE production, or to reduce or eliminate serum IgE levels. As used herein, a reduction in serum IgE level means that the amount of IgE measured in the serum of a subject who has been exposed to an allergen and who has been treated with an IL-4R antagonist, is at least 5%, 10%, 20%, 50%, 80%, or 90% lower than the serum IgE level measured in the same or an equivalent subject that has not been treated with the IL-4 antagonist. In certain embodiments, a reduction in serum IgE level means that no or negligible amounts of allergen-specific IgE are detected in the serum of a subject.

As used herein, the phrases "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., increased IgE production and/or increased allergen-specific immunoglobulin production.

The term "allergen," as used herein, includes any substance, chemical, particle or composition which is capable of stimulating an allergic response in a susceptible individual. Allergens may be contained within or derived from a food item such as, e.g., dairy products (e.g., cow's milk), egg, celery, sesame, wheat, soy, fish, shellfish, sugars (e.g., sugars present on meat such as alpha-galactose), peanuts, other legumes (e.g., beans, peas, soybeans, etc.), and tree nuts. Alternatively, an allergen may be contained within or derived from a non-food item such as, e.g., dust (e.g., containing dust mite), pollen, insect venom (e.g., venom of bees, wasps, mosquitos, fire ants, etc.), mold, animal fur, animal dander, wool, latex, metals (e.g., nickel), household cleaners, detergents, medication, cosmetics (e.g., perfumes, etc.), drugs (e.g., penicillin, sulfonamides, salicylate, etc.), therapeutic monoclonal antibodies (e.g., cetuximab), ragweed, grass and birch. Exemplary pollen allergens include, e.g., tree pollens such as birch pollen, cedar pollen, oak pollen, alder pollen, hornbeam pollen, *aesculus* pollen, willow pollen, poplar pollen, plantanus pollen, *tilia* pollen, *olea* pollen, Ashe juniper pollen, and Alstonia scholaris pollen.

The methods of the present invention comprise administering a pharmaceutical composition comprising an IL-4R antagonist to a subject before, after and/or during allergen exposure. For example, the present invention includes methods comprising administering a pharmaceutical composition comprising an IL-4R antagonist to a subject less than 12 hours, less than 10 hours, less than 8 hours, less than 6 hours, less than 4 hours, less than 2 hours, less than 1 hour, or less than 30 minutes before allergen exposure. In certain embodiments, the pharmaceutical composition comprising an IL-4R antagonist is administered to a subject several days to weeks prior to allergen exposure (e.g., from about 1 day to about 2 weeks before allergen exposure). The present invention also includes methods comprising administering a pharmaceutical composition comprising an IL-4R antagonist to a subject less than 12 hours, less than 10 hours, less than 8 hours, less than 6 hours, less than 4 hours, less than 2 hours, less than 1 hour, or less than 30 minutes after allergen exposure. As used herein the expression "allergen exposure" means any incident, episode or occurrence during which a subject ingests, inhales, touches or otherwise is in direct or indirect contact with an allergen.

The present invention also includes methods comprising administering a pharmaceutical composition comprising an IL-4R antagonist to a subject following the manifestation of one or more allergic symptoms in the subject. For example, the present invention includes methods comprising administering a pharmaceutical composition comprising an IL-4R antagonist to a subject immediately after, 30 minutes after, 1 hour after, 2 hours after, 4 hours after, 6 hours after, 8 hours after, 10 hours after, or 12 hours after the initial manifestation of one or more allergic symptoms in the subject.

The present invention includes methods for treating, preventing or reducing the severity of an allergic reaction, wherein the allergic reaction is triggered by any of the aforementioned allergens or classes of allergens. For example, the present invention includes methods for treating, preventing or reducing the severity of an allergic reaction triggered by consumption or exposure to a food item (e.g., milk, egg, wheat, soy, fish, shellfish, peanut or tree nut). The present invention also includes methods for treating, preventing or reducing the severity of an allergic reaction triggered by a non-food allergen (e.g., insect venom, dust, mold, animal dander, pollen, latex, medication, ragweed, grass, or birch).

The present invention includes methods for treating, preventing or reducing the severity of an allergic reaction comprising administering a therapeutically effective amount of a pharmaceutical composition comprising an IL-4R antagonist to a subject in need thereof, wherein the pharmaceutical composition is administered to the subject in multiple doses, e.g., as part of a specific therapeutic dosing regimen. For example, the therapeutic dosing regimen may comprise administering multiple doses of the pharmaceutical composition to the subject at a frequency of about once a day, once every two days, once every three days, once every four days, once every five days, once every six days, once a week, once every two weeks, once every three weeks, once every four weeks, once a month, once every two months, once every three months, once every four months, or less frequently.

The methods of the present invention, according to certain embodiments, comprise administering to a subject a therapeutically effective amount of a pharmaceutical composition comprising an IL-4R antagonist in combination with a second therapeutic agent. The second therapeutic agent may be an agent selected from the group consisting of, e.g., steroids, antihistamines, decongestants, and anti-IgE agents. As used herein, the phrase "in combination with" means that the pharmaceutical composition comprising an IL-4R antagonist is administered to the subject at the same time as, just before, or just after administration of the second therapeutic agent. In certain embodiments, the second therapeutic agent is administered as a co-formulation with the IL-4R antagonist. In a related embodiment, the present invention includes methods comprising administering a therapeutically effective amount of a pharmaceutical composition comprising an IL-4R antagonist to a subject who is on a background anti-allergy therapeutic regimen. The background anti-allergy therapeutic regimen may comprise a course of administration of, e.g., steroids, antihistamines, decongestants, anti-IgE agents, etc. The IL-4R antagonist may be added on top of the background anti-allergy therapeutic regimen. In some embodiments, the IL-4R antagonist is added as part of a "background step-down" scheme, wherein the background anti-allergy therapy is gradually withdrawn from the subject over time (e.g., in a stepwise fashion) while the IL-4R antagonist is administered the subject at a constant dose, or at an increasing dose, or at a decreasing dose, over time.

Methods for Enhancing the Efficacy and/or Safety of Allergen-Specific Immunotherapy (SIT)

The present invention also includes methods for enhancing the efficacy and/or safety of allergen-specific immunotherapy (SIT). The methods according to this aspect of the invention comprise administering a therapeutically effective amount of a pharmaceutical composition comprising an IL-4R antagonist to a subject just prior to or concurrent with a SIT regimen.

As used herein, the expressions "allergen-specific immunotherapy," "specific immunotherapy," "SIT," "SIT regimen," and the like, refer to the repeated administration of an allergen to a subject over time as means for treating or preventing allergies and allergic reactions, or to reduce or eliminate allergic responses. In a typical SIT regimen, small amounts of allergen are initially administered to an allergic subject, followed by administration of increased amounts of allergen. In certain instances, the SIT regimen comprises at least two consecutive phases: (1) an up-dosing phase, and (2) a maintenance phase. In the up-dosing phase, increasing doses of allergen are administered until an effective and safe dose is achieved. The dose that is established at the end of the up-dosing phase is then administered to the subject throughout the course of the maintenance phase. The duration of the up-dosing phase can be several weeks or several months. In certain embodiments, however, the up-dosing phase is of substantially shorter duration (e.g., less than one week, less than 6 days, less than 5 days, less than 4 days, less than 3 days, or less than 2 days). SIT regimens comprising an up-dosing phase of less than 5 days are sometimes referred to as "Rush" immunotherapy or "Rush SIT." The maintenance phase of an SIT regimen can last several weeks, several months, several years, or indefinitely.

According to this aspect of the invention, the SIT regimen may comprise administration of a food allergen derived from a food item selected from the group consisting of dairy product, egg, wheat, soy, fish, shellfish, peanut and tree nut. Alternatively, the SIT regimen may comprise administration of a non-food allergen selected from the group consisting of insect venom, dust, mold, animal dander, pollen, latex, medication, ragweed, grass, and birch.

According to the methods of the present invention, the IL-4R antagonist can be administered to the subject throughout the entire course of the SIT regimen, or for only a portion of the SIT regimen. For example, the methods of the present invention include administration of a therapeutically effective amount of a pharmaceutical composition comprising an IL-4R antagonist to a subject at a frequency of about once a week, once every two weeks, once every three weeks, once a month, once every two months, once every four months, once every six months, or less frequently, prior to or during the up-dosing phase. In certain embodiments, the pharmaceutical composition comprising an IL-4R antagonist is administered to the subject at a frequency of about once a week, once every two weeks, once every three weeks, once a month, once every two months, once every four months, once every six months, or less frequently, during or after the maintenance phase.

According to the present invention, the efficacy and/or safety of an SIT regimen is "enhanced" if one or more of the following outcomes or phenomena are observed or achieved in a subject: (1) the duration of the up-dosing phase is decreased without compromising efficacy or safety; (2) the duration of the maintenance phase is decreased without compromising efficacy or safety; (3) the number of doses of allergen administered during the up-dosing or maintenance phase is reduced without compromising efficacy or safety; (4) the frequency of allergen administration during the up-dosing or maintenance phase is reduced without compromising efficacy or safety; (5) the dose of allergen administered during the up-dosing or maintenance phase is increased without compromising efficacy or safety; (6) the frequency of allergic responses or adverse side-effects triggered by the SIT regimen is reduced or eliminated; (7) the use of or need for conventional allergy medications (e.g., steroids, antihistamines, decongestants, anti-IgE agents, etc.) is reduced or eliminated during the up-dosing and/or maintenance phases; (8) the level of allergen-induced IgE expression is reduced; and/or (9) the frequency of anaphylactic reactions is reduced or eliminated. The efficacy of an SIT regimen is also deemed to be "enhanced," according to the present invention, if a subject experiences fewer and/or less severe allergic reactions following SIT therapy in combination with IL-4R blockade than with SIT therapy alone.

The present invention also includes methods for weaning a subject off of an SIT regimen. The methods according to this aspect of the invention comprise administering to the subject one or more doses of a pharmaceutical composition comprising an IL-4R antagonist, and gradually reducing the frequency and/or quantity of allergen administered to the subject during the course of the SIT regimen. In certain embodiments, the quantity of IL-4R antagonist is increased while the quantity of allergen administered as part of the SIT regimen is decreased. Preferably, administration of the IL-4R antagonist will allow the SIT regimen to be terminated while still providing adequate protection from unwanted allergic reactions.

Interleukin-4 Receptor Antagonists

The methods of the present invention comprise administering to a subject in need thereof a therapeutic composition comprising an interleukin-4 receptor (IL-4R) antagonist. As used herein, an "IL-4R antagonist" (also referred to herein as an "IL-4Rα antagonist," an "IL-4R blocker," an "IL-4Rα blocker," etc.) is any agent which binds to or interacts with IL-4Rα or an IL-4R ligand, and inhibits or attenuates the normal biological signaling function a type 1 and/or a type 2 IL-4 receptor. Human IL-4Rα has the amino acid sequence of SEQ ID NO: 11. A type 1 IL-4 receptor is a dimeric receptor comprising an IL-4Rα chain and a γc chain. A type 2 IL-4 receptor is a dimeric receptor comprising an IL-4Rα chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists that can be used in the methods of the present invention may function by blocking IL-4-mediated signaling, IL-13-mediated signaling, or both IL-4- and IL-13-mediated signaling. The IL-4R antagonists of the present invention may thus prevent the interaction of IL-4 and/or IL-13 with a type 1 or type 2 receptor.

Non-limiting examples of categories of IL-4R antagonists include small molecule IL-4R antagonists, anti-IL-4R aptamers, peptide-based IL-4R antagonists (e.g., "peptibody" molecules), "receptor-bodies" (e.g., engineered molecules comprising the ligand-binding domain of an IL-4R component), and antibodies or antigen-binding fragments of antibodies that specifically bind human IL-4Rα. As used herein, IL-4R antagonists also include antigen-binding proteins that specifically bind IL-4 and/or IL-13.

Anti-IL-4Rα Antibodies and Antigen-Binding Fragments Thereof

According to certain exemplary embodiments of the present invention, the IL-4R antagonist is an anti-IL-4Rα antibody or antigen-binding fragment thereof. The term "antibody," as used herein, includes immunoglobulin molecules comprising four polypeptide chains, two heavy (H) chains and two light (L) chains inter-connected by disulfide bonds, as well as multimers thereof (e.g., IgM). In a typical antibody, each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-4R antibody (or antigen-binding portion thereof)

may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

The term "antibody," as used herein, also includes multispecific (e.g., bispecific) antibodies. A multispecific antibody or antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antibody or antigen-binding fragment of an antibody of the present invention using routine techniques available in the art. For example, the present invention includes methods comprising the use of bispecific antibodies wherein one arm of an immunoglobulin is specific for IL-4Rα or a fragment thereof, and the other arm of the immunoglobulin is specific for a second therapeutic target or is conjugated to a therapeutic moiety. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

The antibodies used in the methods of the present invention may be human antibodies. The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The antibodies used in the methods of the present invention may be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl.

Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

According to certain embodiments, the antibodies used in the methods of the present invention specifically bind IL-4Rα. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4Rα, as used in the context of the present invention, includes antibodies that bind IL-4Rα or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-4Rα may, however, have cross-reactivity to other antigens, such as IL-4Rα molecules from other (non-human) species.

According to certain exemplary embodiments of the present invention, the IL-4R antagonist is an anti-IL-4Rα antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. No. 7,608,693. In certain exemplary embodiments, the anti-IL-4Rα antibody or antigen-binding fragment thereof that can be used in the context of the methods of the present invention comprises the heavy chain complementarity determining regions (HCDRs) of a heavy chain variable region (HCVR) comprising the amino acid sequence of SEQ ID NO:1 and the light chain complementarity determining regions (LCDRs) of a light chain variable region (LCVR) comprising the amino acid sequence of SEQ ID NO:2. According to certain embodiments, the anti-IL-4Rα antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO:3; the HCDR2 comprises the amino acid sequence of SEQ ID NO:4; the HCDR3 comprises the amino acid sequence of SEQ ID NO:5; the LCDR1 comprises the amino acid sequence of SEQ ID NO:6; the LCDR2 comprises the amino acid sequence of SEQ ID NO:7; and the LCDR3 comprises the amino acid sequence of SEQ ID NO:8. In yet other embodiments, the anti-IL-4R antibody or antigen-binding fragment thereof comprises an HCVR comprising SEQ ID NO:1 and an LCVR comprising SEQ ID NO:2. According to certain exemplary embodiments, the methods of the present invention comprise the use of the anti-IL-4Rα antibody referred to and known in the art as dupilumab, or a bioequivalent thereof.

Other anti-IL-4Rα antibodies that can be used in the context of the methods of the present invention include, e.g., the antibody referred to and known in the art as AMG317 (Corren et al., 2010, *Am J Respir Crit Care Med.*, 181(8): 788-796), or any of the anti-IL-4Rα antibodies as set forth in U.S. Pat. No. 7,186,809, U.S. Pat. No. 7,605,237, U.S. Pat. No. 7,608,693, or U.S. Pat. No. 8,092,804.

The anti-IL-4Rα antibodies used in the context of the methods of the present invention may have pH-dependent binding characteristics. For example, an anti-IL-4Rα antibody for use in the methods of the present invention may exhibit reduced binding to IL-4Rα at acidic pH as compared to neutral pH. Alternatively, an anti-IL-4Rα antibody of the invention may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-4Rα at acidic pH as compared to neutral pH" is expressed in terms of a ratio of the $K_D$ value of the antibody binding to IL-4Rα at acidic pH to the $K_D$ value of the antibody binding to IL-4Rα at neutral pH (or vice versa). For example, an antibody or antigen-binding fragment thereof may be regarded as exhibiting "reduced binding to IL-4Rα at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

Pharmaceutical Compositions

The present invention includes methods which comprise administering an IL-4R antagonist to a subject wherein the IL-4R antagonist is contained within a pharmaceutical composition. The pharmaceutical compositions of the invention may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used in the context of the present invention are disclosed, e.g., in US Patent Application Publication No. 2012/0097565.

Dosage

The amount of IL-4R antagonist (e.g., anti-IL-4Rα antibody) administered to a subject according to the methods of the present invention is, generally, a therapeutically effective amount. As used herein, the phrase "therapeutically effective amount" means an amount of IL-4R antagonist that results in one or more of: (a) a reduction in the severity or duration of an allergic reaction; (b) the alleviation of one or more symptoms or indicia of an allergic reaction; (c) prevention or alleviation of anaphylaxis; (d) a reduction in serum IgE level; (e) a reduction in the use or need for conventional allergy therapy (e.g., reduced or eliminated use of antihistamines, decongestants, nasal or inhaled steroids, anti-IgE treatment, epinephrine, etc.); and (f) a reduced frequency of allergic responses to allergen-specific immunotherapy (SIT).

In the case of an anti-IL-4Rα antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-4R antibody. In certain embodiments, 300 mg of an anti-IL-4R antibody is administered.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. IL-4R Blockade Prevents Systemic Anaphylaxis in a Mouse Model of Peanut Allergy In this Example, the effect of IL-4Rα blockade on peanut-induced anaphylaxis in a mouse model was assessed. An outline of the experimental protocol is shown in FIG. 1A. Briefly, three groups of 5 C57BL/6 mice were each sensitized with 100 μg of crude peanut extract and Alum (2 mg/ml) administered by subcutaneous injection on Day 0, followed by a boost injection on Day 14. On Day 28 a challenge injection of 50 μg of peanut extract was administered intravenously. The first group of mice received no treatment. The second group of mice were administered an anti-mouse IL-4Rα antibody ("anti-mIL-4Rα") subcutaneously at a dose of 25 mg/kg on Day 13 and Day 27. The third group of mice received an isotype control antibody on Day 13 and Day 27. The anti-mIL-4Rα antibody used in this and the following Examples was an antibody comprising an HCVR with an amino acid sequence of SEQ ID NO:9 and an LCVR with an amino acid sequence comprising SEQ ID NO:10.

Systemic anaphylaxis in this model manifests as a drop in core temperature. Therefore, to assess the extent of anaphylaxis in this experimental system, mouse core temperature was measured over the course of 180 minutes following the challenge injection. Results are shown in FIG. 1B. Untreated mice and mice receiving isotype control antibody exhibited a rapid decrease in core body temperature at 30 minutes after challenge, indicating an anaphylactic reaction. Core temperature in the control mice gradually increased to baseline by 180 minutes post-challenge. By contrast, mice that received anti-m IL-4Rα treatment exhibited only a slight decrease in core body temperature at 30 minutes post-challenge which returned to normal by the 60 minute time point. The difference in core body temperature change between anti-mIL-4Rα-treated mice and controls at the 30 minute time point was statistically significant (P<0.0001).

Figure 2:
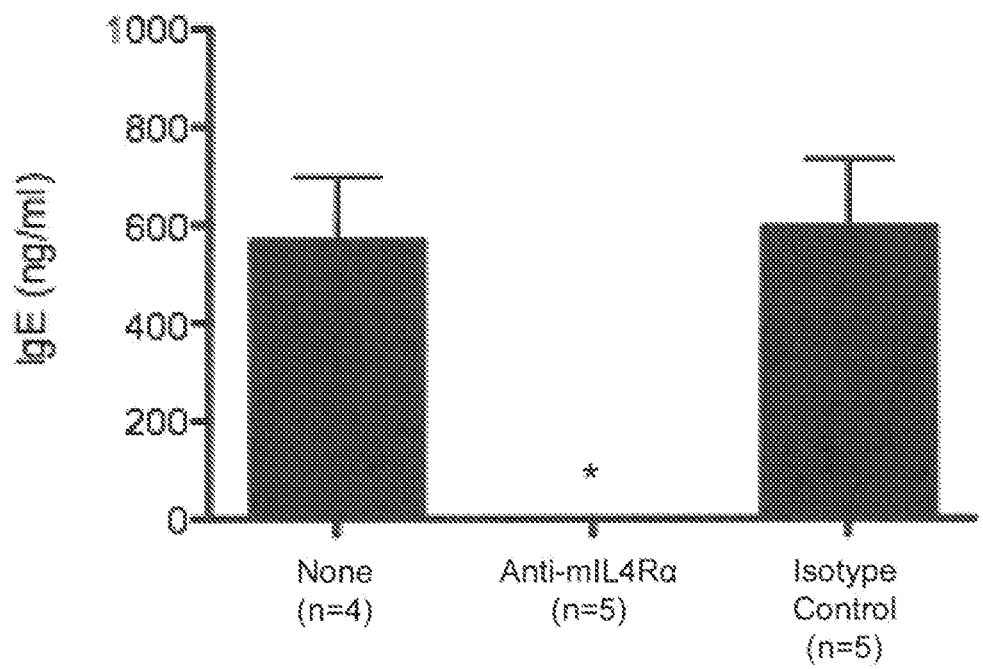
FIG. 2 shows the IgE levels of the three groups of mice referred to in FIG. 1 following peanut extract challenge.

The terminal IgE level was also measured for each experimental group (FIG. 2). As shown, IL-4Rα blockade significantly decreased total IgE levels below the limit of detection as compared to untreated and isotype control-treated animals.

Figure 3:
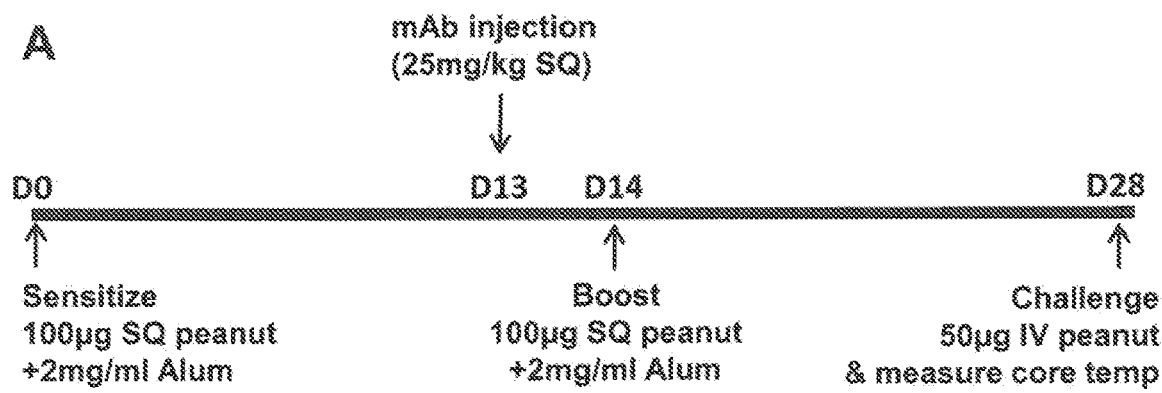
FIG. 3 Panel A depicts the time course of a peanut allergy mouse model in which a single dose of an anti-IL-4Rα antibody was administered to the mice on Day 13. Panel B shows the extent of anaphylaxis in three groups of experimental mice, assessed in terms of core temperature decrease over time following IV peanut extract challenge. Mice receiving no antibody are designated with grey filled circles; mice receiving anti-IL-4Rα antibody are designated with black filled squares; mice receiving isotype control antibody are designated with open squares.
Figure 3:
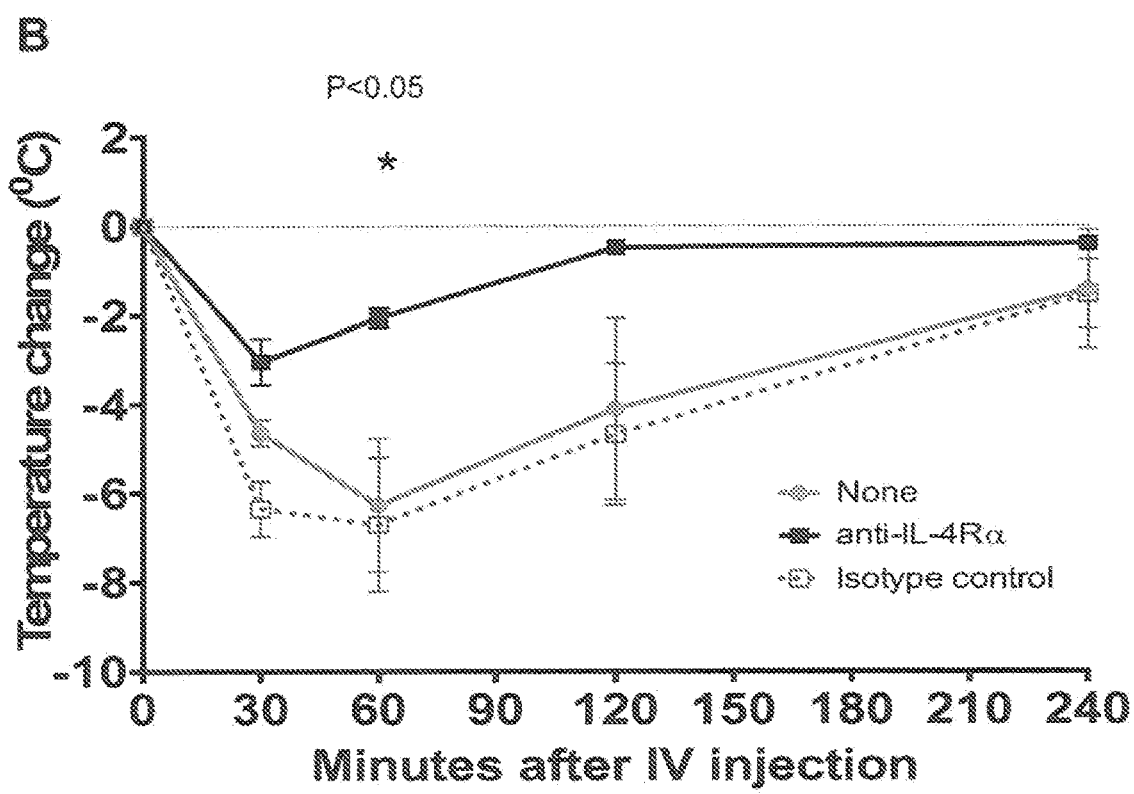
Figure 4:
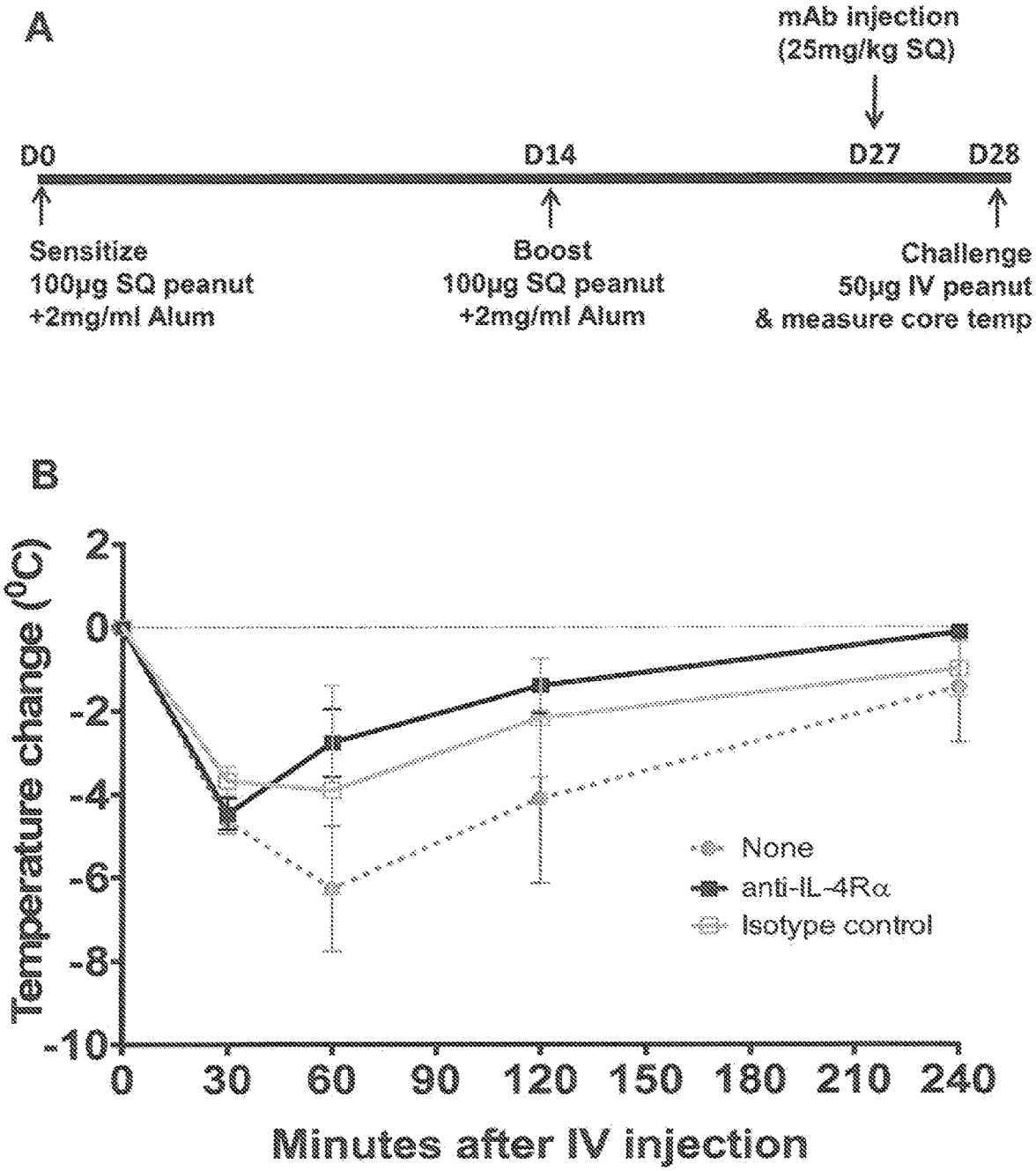
FIG. 4 Panel A depicts the time course of a peanut allergy mouse model in which a single dose of an anti-IL-4Rα antibody was administered to the mice on Day 27. Panel B shows the extent of anaphylaxis in three groups of experimental mice, assessed in terms of core temperature decrease over time following IV peanut extract challenge. Mice receiving no antibody are designated with grey filled circles; mice receiving anti-IL-4Rα antibody are designated with black filled squares; mice receiving isotype control antibody are designated with open squares.

The foregoing experiments involved two separate doses of anti-mIL-4Rα antibody (administered on D13 and D27). A second set of experiments was next conducted to assess the effect of a single administration on either Day 13 or Day 27 in the same peanut allergy model. An outline of the experimental protocol is shown in FIG. 3A (D13 administration) and FIG. 4A (D27 administration). Results are shown in FIGS. 3B and 4B, respectively. Mice receiving a single administration of anti-mIL-4Rα antibody on Day 13 exhibited significantly less anaphylaxis as compared to untreated and control-treated animals (see FIG. 3B), however, the protective effect was not as pronounced as in the two-dose administration experiment (FIG. 1B). The protective effect of anti-IL-4Rα treatment was substantially attenuated in the mice receiving single dose of antibody on Day 27 (see FIG. 4B).

Figure 5:
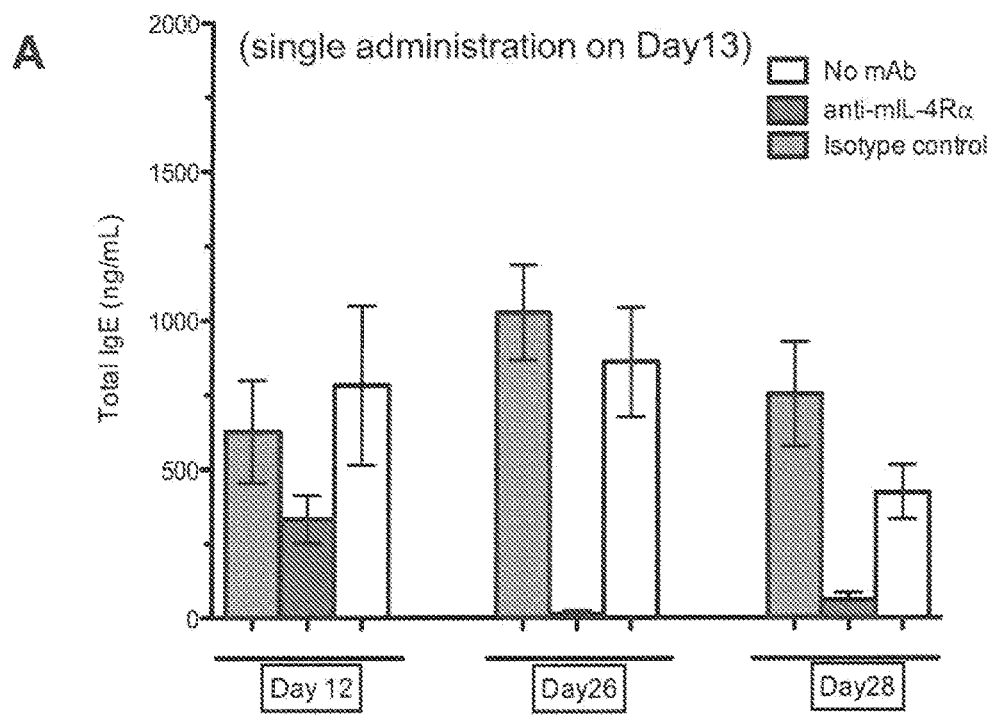
FIG. 5 shows the total IgE levels in the three treatment groups of FIGS. 3 and 4 (no mAb treatment, anti-IL-4Rα treatment, and isotype control-treated mice) on Days 12, 26 and 28 of the respective experimental time courses. Panel A shows the results of the experiments in which a single dose of antibody was administered on Day 13; Panel B shows the results of the experiments in which a single dose of antibody was administered on Day 27.
Figure 5:
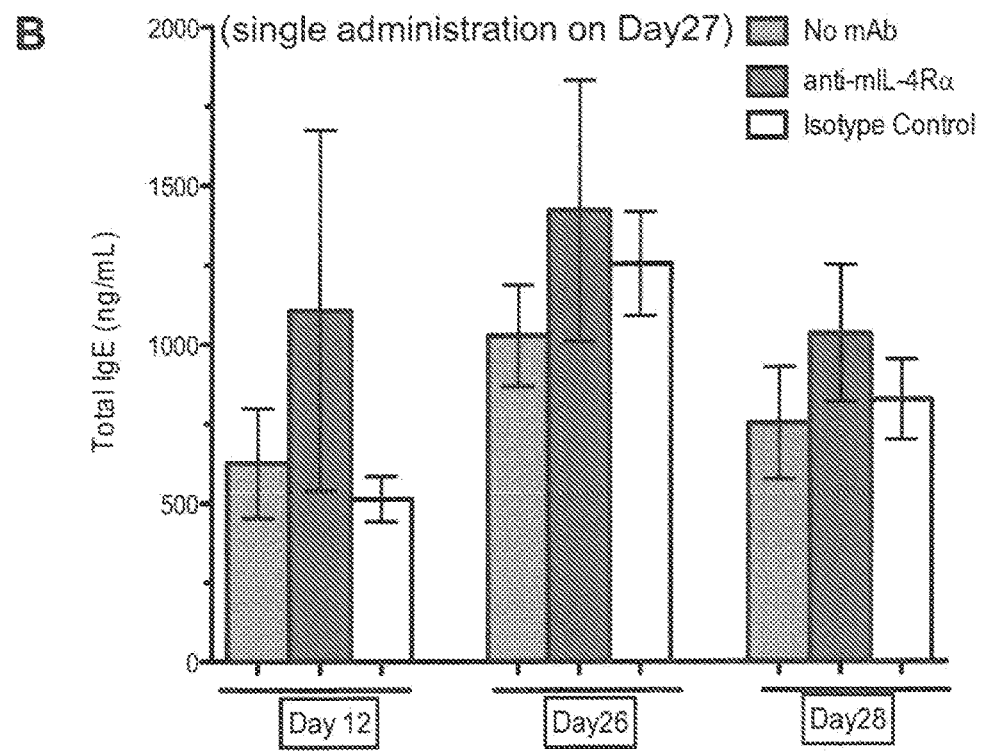

In the single administration experiments, IgE levels were measured in samples taken from the animals at Day 12, Day 26 and Day 28. Results are shown in FIG. 5A (Day13 administration) and FIG. 5B (Day 27 administration). Importantly, the effect of anti-m IL-4Rα antibody on systemic anaphylaxis correlated with the degree of IgE inhibition. The reduction in IgE levels was not immediate following anti-mIL-4Rα treatment but appeared to require about 13 days from the time of antibody administration until the time at which IgE levels were fully suppressed. This Example therefore supports a role for IL-4R antagonism in preventing allergic reactions.

Example 2: Use of IL-4R Blockade in a Peanut Specific Immunotherapy Model

The purpose of this Example was to determine the effects of IL-4Rα blockade when added to an allergen-specific immunotherapy (SIT) regimen. For these experiments, a mouse peanut specific immunotherapy model was developed based in part on the model of Kulis et al., *J. Allergy Clin. Immunol.* 127(1):81-88 (2011). Two sets of experiments were conducted, as described below.

Figure 6:
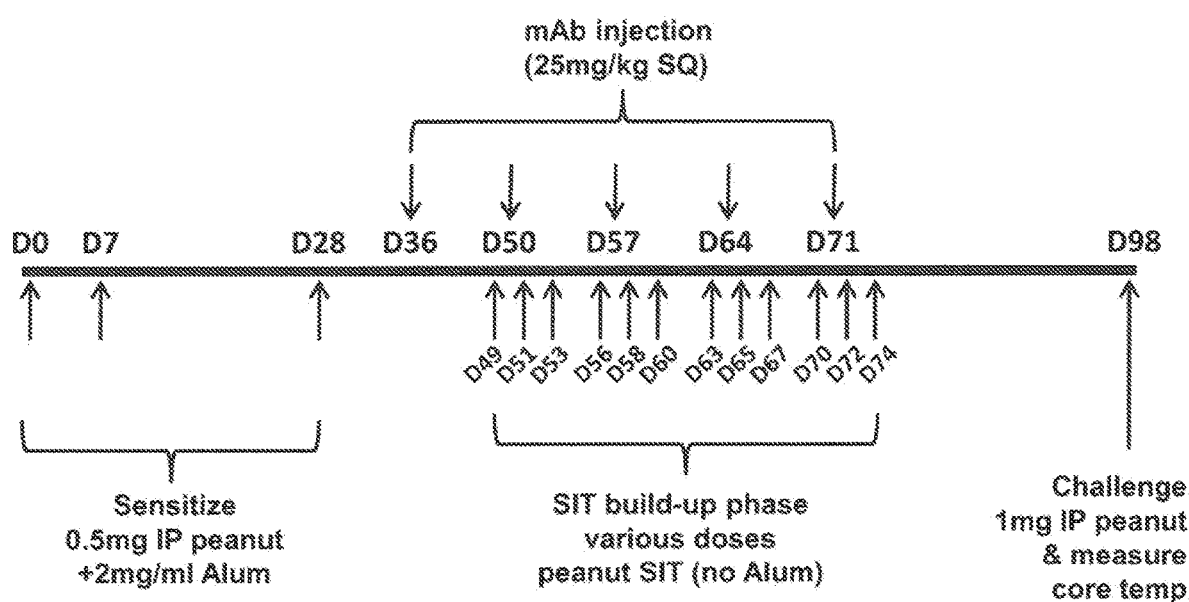
FIG. 6 depicts the time course of a peanut specific immunotherapy mouse model comprising a sensitizing phase, a SIT build-up phase, and a peanut extract challenge. Five antibody injections were administered to the mice on the days indicated.

An outline of the experimental protocol used in the first set of experiments is shown in FIG. 6. Four groups of mice were used in these experiments. Three of the four groups of mice were subjected to a peanut specific immunotherapy regimen comprising a Sensitization Phase, a Build-up Phase, and a Challenge. The Sensitization Phase consisted of administration of 0.5 mg peanut extract+2 mg Alum administered intraperitoneally on Days 0, 7 and 28. The Build-up Phase consisted of twelve separate administrations of various doses of peanut extract without Alum on Days 49, 51, 53, 56, 58, 60, 63, 65, 67, 70, 72 and 74. The Challenge consisted of administration of 1 mg of peanut extract on Day 98.

The various treatment groups for these experiments were as follows: Group A received no immunotherapy and no antibody ("No IT"); Group B received immunotherapy only, without antibody ("IT"); Group C received immunotherapy plus isotype control antibody on Days 36, 50, 57, 64 and 71 ("IT+isotype control"); and Group D received immunotherapy plus anti-mIL-4Rα antibody (25 mg/kg, subcutaneous) on Days 36, 50, 57, 64 and 71 ("IT+anti-IL-4Rα"). The anti-mIL-4Rα antibody used in these experiments was the same antibody as used in Example 1, herein.

Figure 7:
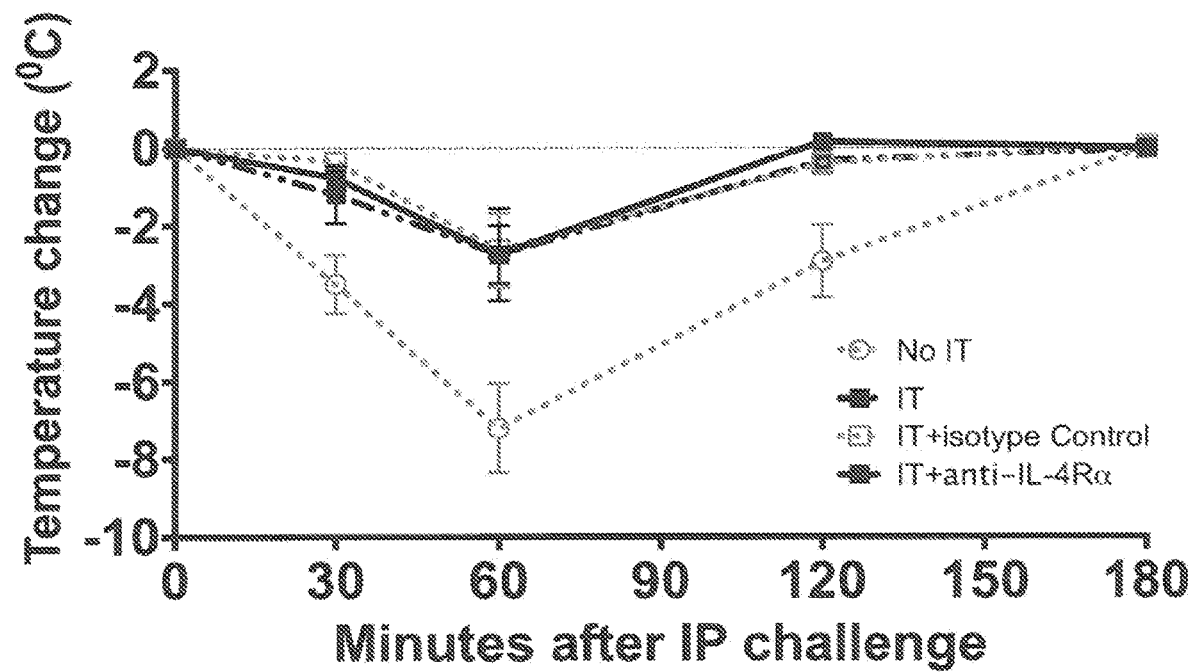
FIG. 7 shows the extent of anaphylaxis in three groups of experimental mice subjected to the peanut specific immunotherapy regimen illustrated in FIG. 6, as well as a no immunotherapy control group. Results are assessed in terms of core temperature decrease over time following peanut extract challenge. Mice subjected to challenge but receiving no immunotherapy are designated with open circles and dashed lines ("No IT"); mice receiving immunotherapy but no antibody are designated with closed squares and dashed lines ("IT"); mice receiving immunotherapy and isotype control antibody are designated with open squares and dashed lines ("IT+isotype control"); mice receiving immunotherapy and anti-IL-4Rα antibody are designated with closed squares and solid lines ("IT+anti-IL-4Rα).
Figure 8:
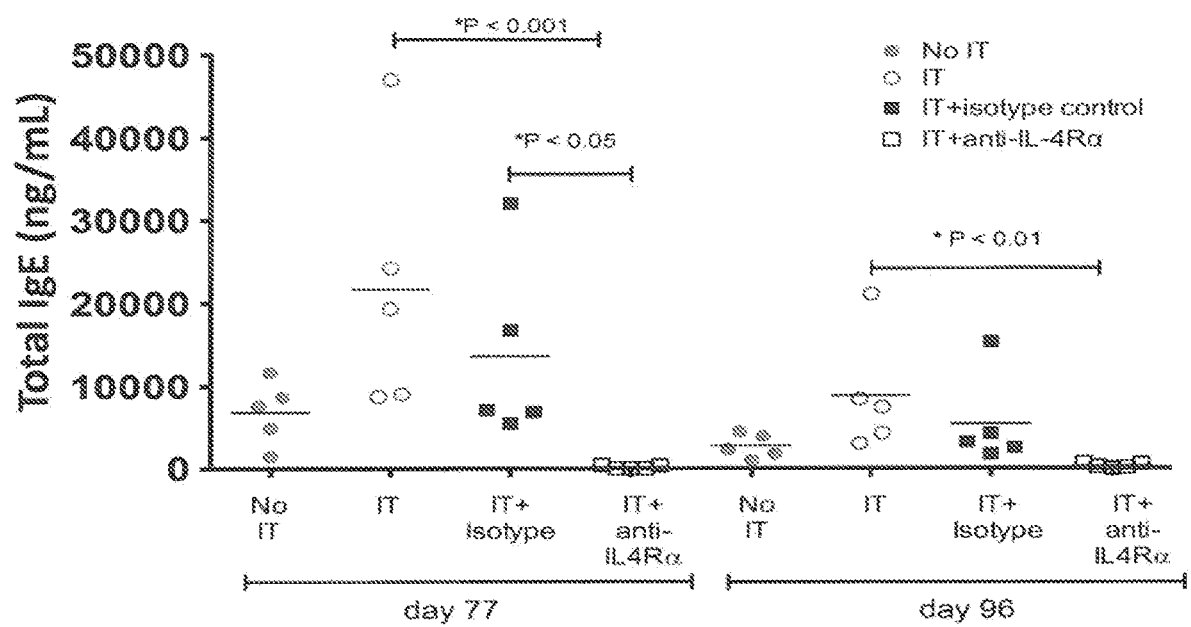
FIGS. 8, 9, 10 and 11 show the total IgE levels (FIG. 8), peanut-specific IgG1 levels (FIG. 9), peanut-specific IgG2a levels (FIG. 10), and hIgG levels (FIG. 11), in three groups of experimental mice subjected to the peanut specific immunotherapy regimen illustrated in FIG. 6, as well as a no immunotherapy control group. The various immunoglobulin levels at Day 77 and Day 96 are shown. Mice subjected to challenge but receiving no immunotherapy are designated with closed circles ("No IT"); mice receiving immunotherapy but no antibody are designated with open circles ("IT"); mice receiving immunotherapy and isotype control antibody are designated with closed squares ("IT+isotype control"); mice receiving immunotherapy and anti-IL-4Rα antibody are designated with open squares ("IT+anti-IL-4Rα). Each symbol represents the measured level in an individual mouse.
Figure 9:
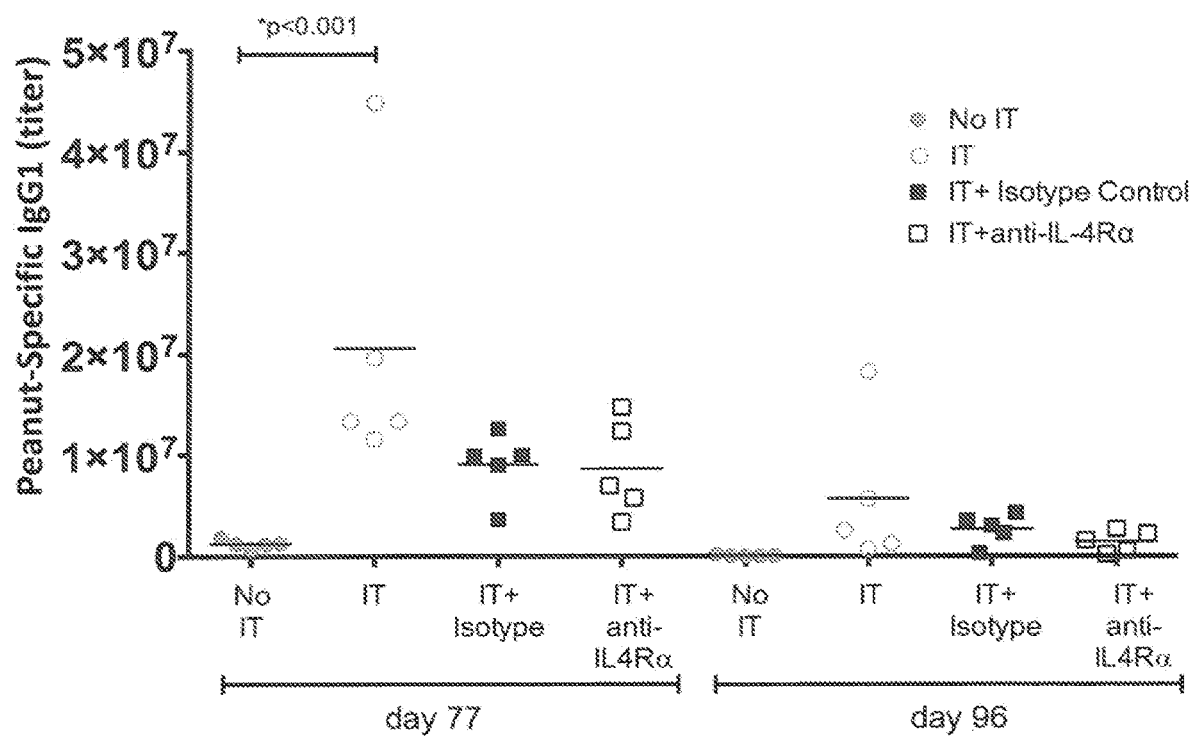
Figure 10:
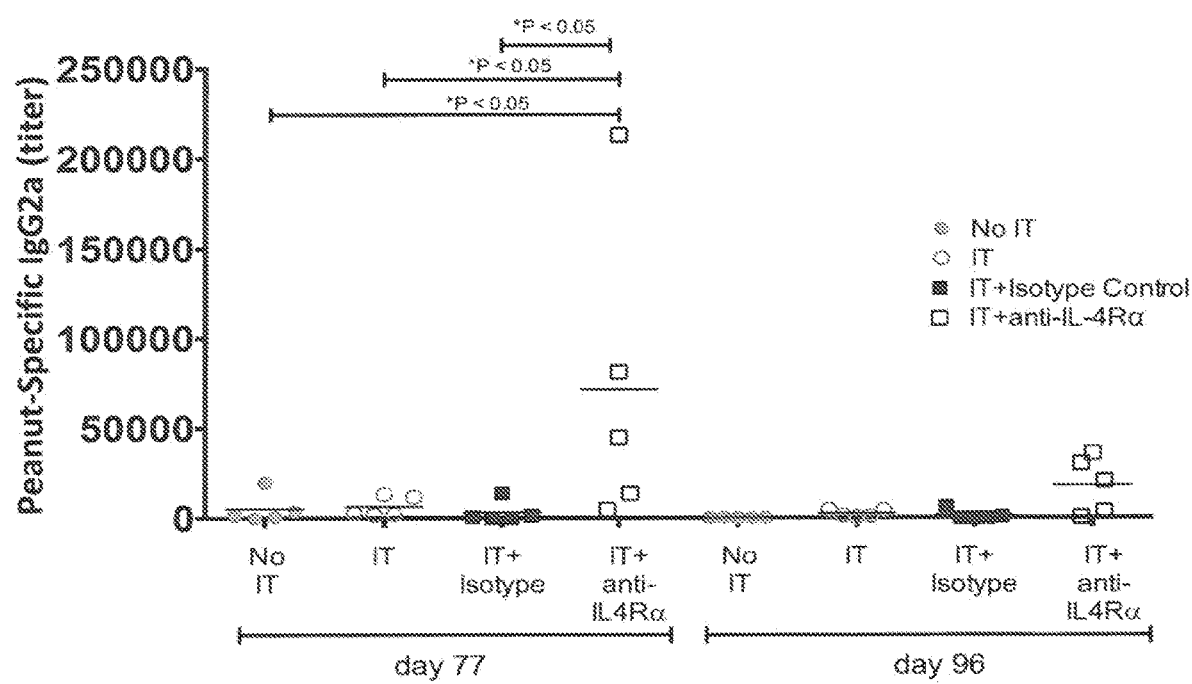
Figure 11:
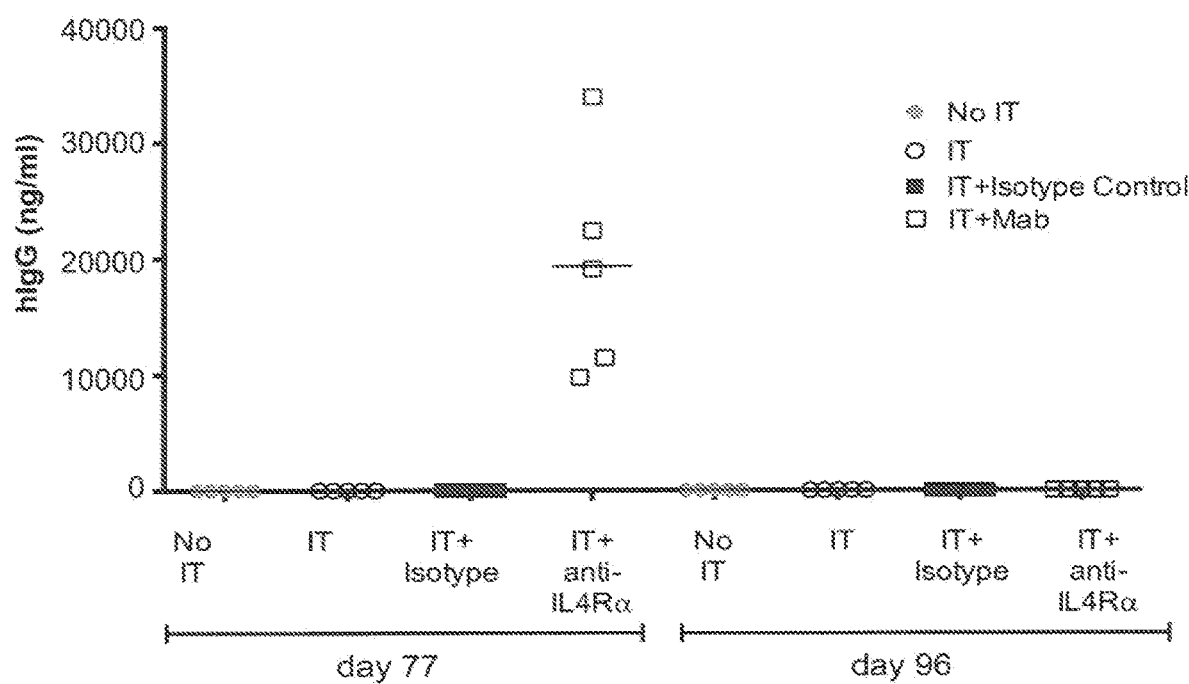

To assess the extent of anaphylaxis in this system, mouse core temperature was measured over the course of 180 minutes following the challenge injection. In addition, serum samples were collected throughout the experiment (at Days 35, 46, 77 and 98) for immunoglobulin measurements. Anaphylaxis results are shown in FIG. 7. Total IgE, IgG1, IgG2a and IgG levels at Days 77 and 96 are shown in FIGS. 8, 9, 10 and 11, respectively.

The results of these experiments show that allergen-specific immunotherapy by itself protects against peanut-induced systemic anaphylaxis in this model (see FIG. 7). Importantly, administration of an anti-IL-4Rα antibody did not interfere with the observed protective effects of SIT. In addition, a trend towards increased IgE induced by SIT was observed in IT-only and IT+isotype control treated animals. By contrast, IgE production was blocked in anti-IL-4Rα-treated animals (see FIG. 8). A tendency toward increased peanut-specific IgG1 titers was observed in animals treated with immunotherapy (with or without antibody treatment), however statistical significance was only observed in the IT animals at Day 77 (see FIG. 9). IL-4Rα blockade was also observed to cause an increase in peanut-specific IgG2a (see FIG. 10). The results from this first set of experiments provide experimental support for the use of IL-4R blockade as a means to potentially improve the efficacy and safety of allergen-specific immunotherapy.

Figure 12:
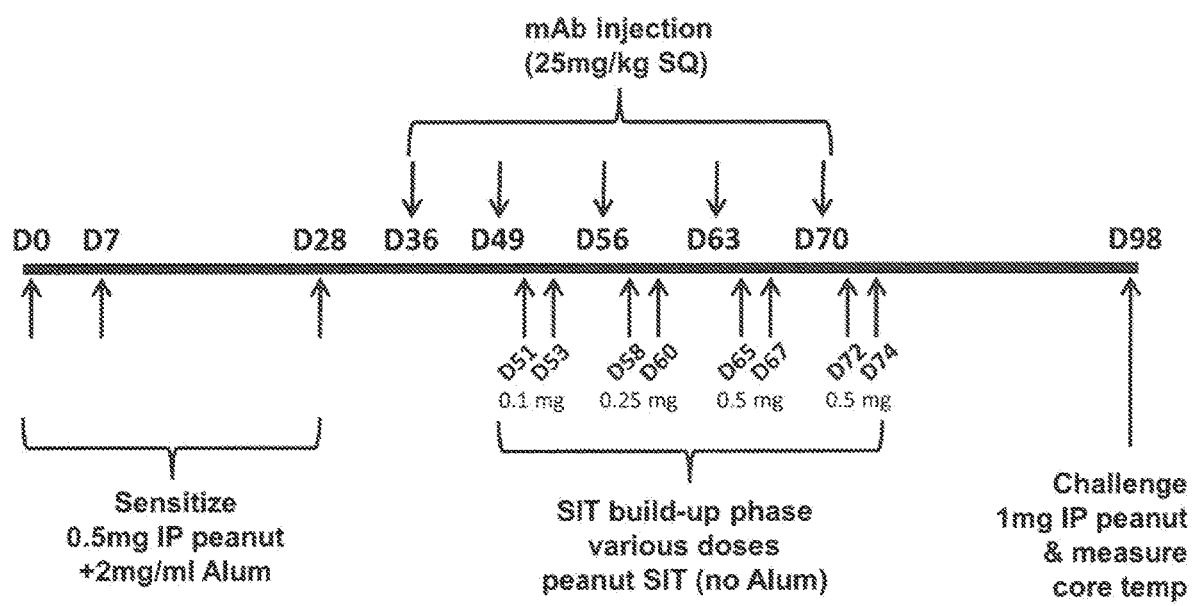
FIG. 12 depicts the time course of a variation of the peanut specific immunotherapy mouse model of FIG. 6, in which fewer doses (8 versus 12) of peanut extract were administered during the build-up phase as indicated. Five antibody injections were administered to the mice on the days indicated.

A second set of experiments was next conducted to determine the effect of IL-4R blockade in a SIT regimen with fewer allergen doses during the Build-up Phase. An outline of the experimental protocol used in this second set of experiments is shown in FIG. 12. As before, four groups of mice were used in these experiments. Three of the four groups of mice were subjected to a peanut specific immunotherapy regimen identical to the regimen used in the first set of experiments except that fewer doses of allergen were administered during the Build-up Phase. In particular, the Build-up Phase in these experiments consisted of only eight (as opposed to twelve) separate administrations of various doses of peanut extract without Alum on Days 51 and 53 (0.1 mg), 58 and 60 (0.25 mg), 65 and 67 (0.5 mg), and 72 and 74 (0.5 mg).

Figure 13:
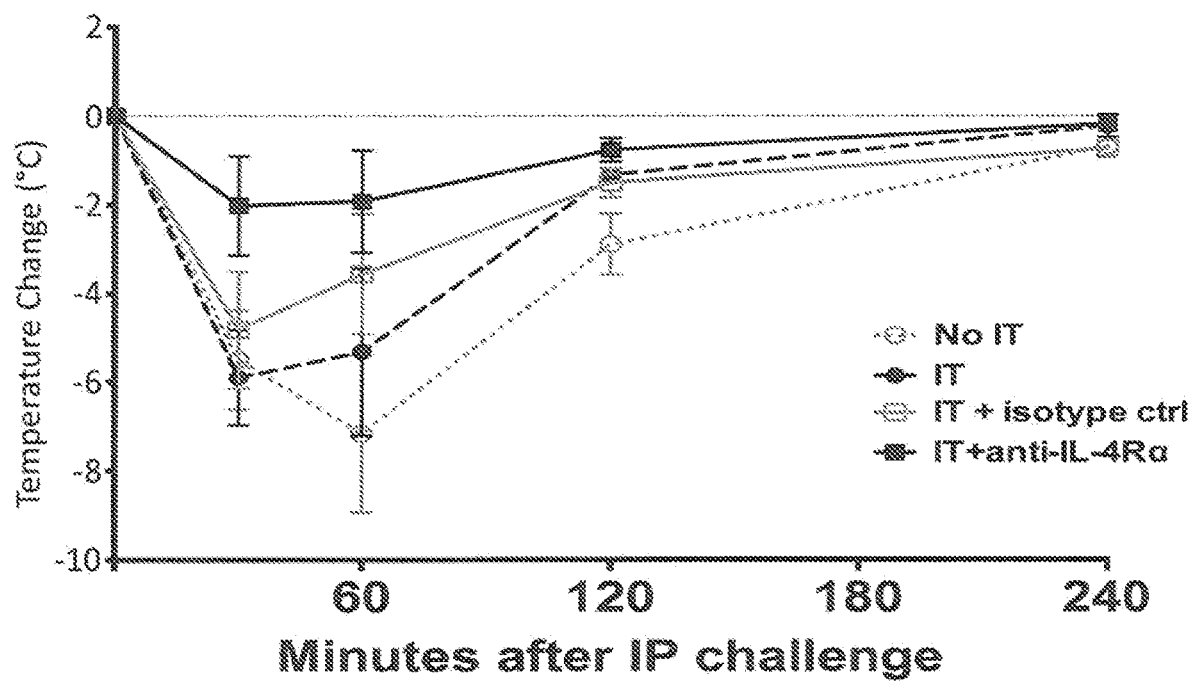
FIG. 13 shows the extent of anaphylaxis in three groups of experimental mice subjected to the peanut specific immunotherapy regimen illustrated in FIG. 12, as well as a no immunotherapy control group. Results are assessed in terms of core temperature decrease over time following peanut extract challenge. Treatment groups are the same as in FIG. 6.

Again, four treatment groups were used ("No IT", "IT only", "IT+isotype control"; and "IT+anti-IL-4Rα"). Antibody was administered at the same dose as before (25 mg/kg SQ), however injections were administered on Days 36, 49, 56, 63 and 70 (as opposed to Days 36, 50, 57, 64 and 71 in the first set of experiments). The extent of anaphylaxis was determined by measuring mouse core temperature over the course of 240 minutes following the challenge injection. Results are shown in FIG. 13.

In these experiments, less frequent allergen administration during the Build-up Phase was less protective against anaphylaxis as compared to the more frequent dosing regimen used in the first set of experiments (8 doses versus 12). In particular, a substantial drop in core body temperature in the IT and IT+isotype control mice during the first 60 minutes after allergen Challenge was observed which was only slightly less severe than what was observed in the "No IT" mice. By contrast, only a mild anaphylactic response (i.e., slight decrease in core body temperature) was observed in the anti-IL-4Rα-treated mice. The Build-up Phase in this model may be considered analogous to the maintenance phase in conventional SIT regimens in humans. The results from this Example therefore indicate that IL-4R blockade can substantially improve the safety of allergen-specific immunotherapy regimens by allowing for reduced maintenance phase dosing. Less frequent allergen dosing would also be more convenient and would result in greater patient compliance in SIT regimens.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating or reducing the severity of an allergic reaction, the method comprising administering a therapeutically effective amount of a pharmaceutical composition comprising an interleukin-4 receptor (IL-4R) antagonist to a subject in need thereof, wherein the allergic reaction is triggered by a non-food allergen, wherein the IL-4R antagonist is an antibody or antigen-binding fragment thereof that binds IL-4R, wherein the antibody or antigen-binding fragment thereof comprises three heavy chain complementarity determining regions (HCDR1, HCDR2 and HCDR3) and three light chain complementarity determining regions (LCDR1, LCDR2 and LCDR3), wherein the HCDR1 comprises the amino acid sequence of SEQ ID NO:3, the HCDR2 comprises the amino acid sequence of SEQ ID NO:4, the HCDR3 comprises the amino acid sequence of SEQ ID NO:5, the LCDR1 comprises the amino acid sequence of SEQ ID NO:6, the LCDR2 comprises the amino acid sequence of SEQ ID NO:7, and the LCDR3 comprises the amino acid sequence of SEQ ID NO:8.

2. The method of claim 1, wherein the pharmaceutical composition is administered to the subject before allergen exposure.

3. The method of claim 2, wherein the pharmaceutical composition is administered to the subject less than 4 hours before allergen exposure.

4. The method of claim 1, wherein the pharmaceutical composition is administered to the subject during or after allergen exposure.

5. The method of claim 4, wherein the pharmaceutical composition is administered to the subject less than 4 hours after allergen exposure.

6. The method of claim 4, wherein the pharmaceutical composition is administered to the subject following the manifestation of one or more allergic symptoms in the subject.

7. The method of claim 6, wherein the pharmaceutical composition is administered to the subject less than 4 hours after manifestation of one or more allergic symptoms in the subject.

8. The method of claim 6, wherein the allergic symptoms are selected from the group consisting of urticaria, angioedema, rhinitis, asthma, vomiting, respiratory compromise, swollen lips, swollen tongue, and reduced blood pressure.

9. The method of claim 1, wherein the allergic reaction is anaphylaxis.

10. The method of claim 1, wherein the non-food allergen is selected from the group consisting of dust, pollen, insect venom, mold, animal fur, animal dander, wool, latex, metals, household cleaners, detergents, drugs, therapeutic monoclonal antibodies, ragweed, grass and birch.

11. The method of claim 1, wherein the pharmaceutical composition is administered to the subject as part of a therapeutic dosing regimen comprising once a week, once every two weeks, once every three weeks, or once a month dosing of the pharmaceutical composition.

12. The method of claim 1, wherein the pharmaceutical composition is administered to the subject in combination with a second therapeutic agent selected from the group consisting of steroids, antihistamines, decongestants, and anti-IgE agents.

13. The method of claim 1, wherein the IL-4R antagonist is an antibody or antigen-binding fragment thereof that binds IL-4Ra and prevents the interaction of IL-4 and/or IL-13 with a type 1 or type 2 IL-4 receptor.

14. The method of claim 13, wherein the antibody or antigen-binding fragment thereof prevents the interaction of IL-4 with both type 1 and type 2 IL-4 receptors.

15. The method of claim 1, wherein the antibody or antigen-binding fragment thereof comprises a heavy chain variable region (HCVR) comprising the amino acid sequence of SEQ ID NO: 1 and a light chain variable region (LCVR) comprising the amino acid sequence of SEQ ID NO: 2.

16. The method of claim 1, wherein the IL-4R antagonist is dupilumab or a bioequivalent thereof.

17. The method of claim 1, wherein the pharmaceutical composition is administered subcutaneously.

18. The method of claim 1, wherein the pharmaceutical composition is contained in a syringe or a pen delivery device.

19. The method of claim 18, wherein the pharmaceutical composition is contained in a syringe.

20. The method of claim 18, wherein the pharmaceutical composition is contained in a pen delivery device.

21. The method of claim 20, wherein the pen delivery device is prefilled.

22. The method of claim 10, wherein the non-food allergen is grass.

23. The method of claim 1, wherein the pharmaceutical composition comprises from 50 mg to 600 mg of the IL-4R antagonist.

24. The method of claim 23, wherein the pharmaceutical composition comprises 300 mg of the IL-4R antagonist.

* * * * *

SEQUENCE LISTING

```
<160> NUMBER OF SEQ ID NOS: 11

<210> SEQ ID NO 1
<211> LENGTH: 124
<212> TYPE: PRT
<213> ORGANISM: Artificial Sequence
<220> FEATURE:
<223> OTHER INFORMATION: HCVR

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 2
<211> LENGTH: 112
<212> TYPE: PRT
<213> ORGANISM: Artificial Sequence
<220> FEATURE:
<223> OTHER INFORMATION: LCVR

<400> SEQUENCE: 2
```

```
Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu Tyr Ser
            20                  25                  30

Ile Gly Tyr Asn Tyr Leu Asp Trp Tyr Leu Gln Lys Ser Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 3
<211> LENGTH: 8
<212> TYPE: PRT
<213> ORGANISM: Artificial Sequence
<220> FEATURE:
<223> OTHER INFORMATION: HCDR1

<400> SEQUENCE: 3

```
Gly Phe Thr Phe Arg Asp Tyr Ala
1               5
```

<210> SEQ ID NO 4
<211> LENGTH: 8
<212> TYPE: PRT
<213> ORGANISM: Artificial Sequence
<220> FEATURE:
<223> OTHER INFORMATION: HCDR2

<400> SEQUENCE: 4

```
Ile Ser Gly Ser Gly Gly Asn Thr
1               5
```

<210> SEQ ID NO 5
<211> LENGTH: 18
<212> TYPE: PRT
<213> ORGANISM: Artificial Sequence
<220> FEATURE:
<223> OTHER INFORMATION: HCDR3

<400> SEQUENCE: 5

```
Ala Lys Asp Arg Leu Ser Ile Thr Ile Arg Pro Arg Tyr Tyr Gly Leu
1               5                   10                  15

Asp Val
```

<210> SEQ ID NO 6
<211> LENGTH: 11
<212> TYPE: PRT
<213> ORGANISM: Artificial Sequence
<220> FEATURE:
<223> OTHER INFORMATION: LCDR1

<400> SEQUENCE: 6

```
Gln Ser Leu Leu Tyr Ser Ile Gly Tyr Asn Tyr
1               5                   10
```

<210> SEQ ID NO 7
<211> LENGTH: 3

```
<212> TYPE: PRT
<213> ORGANISM: Artificial Sequence
<220> FEATURE:
<223> OTHER INFORMATION: LCDR2

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: LCDR3

<400> SEQUENCE: 8

Met Gln Ala Leu Gln Thr Pro Tyr Thr
1               5

<210> SEQ ID NO 9
<211> LENGTH: 117
<212> TYPE: PRT
<213> ORGANISM: Artificial Sequence
<220> FEATURE:
<223> OTHER INFORMATION: HCVR mouse surrogate

<400> SEQUENCE: 9

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asp Tyr
            20                  25                  30

Asn Ile His Trp Val Lys Gln Ser His Gly Lys Ser Leu Glu Trp Ile
        35                  40                  45

Gly Tyr Ile Tyr Pro Asn Asn Gly Asp Asn Gly Tyr Asn Gln Lys Phe
    50                  55                  60

Arg Gly Lys Ala Thr Leu Thr Val Asp Lys Ser Ser Thr Ala Tyr
65                  70                  75                  80

Met Glu Leu Arg Ser Leu Thr Ser Asp Asp Ser Ala Val Tyr Tyr Cys
                85                  90                  95

Ala Arg Gly Arg Leu Arg Tyr Phe Asp Val Trp Gly Thr Gly Thr Thr
            100                 105                 110

Val Thr Val Ser Ser
        115

<210> SEQ ID NO 10
<211> LENGTH: 111
<212> TYPE: PRT
<213> ORGANISM: Artificial Sequence
<220> FEATURE:
<223> OTHER INFORMATION: LCVR mouse surrogate

<400> SEQUENCE: 10

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly His Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60
```

```
Arg Phe Ser Gly Ser Gly Ser Arg Thr Asp Phe Thr Leu Thr Leu Asp
 65                  70                  75                  80

Pro Val Glu Ala Asp Asp Ala Ala Thr Tyr Tyr Cys Gln Gln Tyr Asn
                 85                  90                  95

Glu Asp Pro Pro Thr Phe Gly Ser Gly Thr Lys Leu Glu Ile Lys
            100                 105                 110

<210> SEQ ID NO 11
<211> LENGTH: 207
<212> TYPE: PRT
<213> ORGANISM: Artificial Sequence
<220> FEATURE:
<223> OTHER INFORMATION: hIL-4Ralpha

<400> SEQUENCE: 11

Met Lys Val Leu Gln Glu Pro Thr Cys Val Ser Asp Tyr Met Ser Ile
  1               5                  10                  15

Ser Thr Cys Glu Trp Lys Met Asn Gly Pro Thr Asn Cys Ser Thr Glu
                 20                  25                  30

Leu Arg Leu Leu Tyr Gln Leu Val Phe Leu Leu Ser Glu Ala His Thr
             35                  40                  45

Cys Ile Pro Glu Asn Asn Gly Gly Ala Gly Cys Val Cys His Leu Leu
 50                  55                  60

Met Asp Asp Val Val Ser Ala Asp Asn Tyr Thr Leu Asp Leu Trp Ala
 65                  70                  75                  80

Gly Gln Gln Leu Leu Trp Lys Gly Ser Phe Lys Pro Ser Glu His Val
                 85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
            115                 120                 125

Tyr Asn His Leu Thr Tyr Ala Val Asn Ile Trp Ser Glu Asn Asp Pro
        130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
            195                 200                 205
```